(12) United States Patent
Castor

(10) Patent No.: US 10,258,635 B2
(45) Date of Patent: Apr. 16, 2019

(54) FORMULATIONS AND COMPOSITIONS OF VITAMIN D ANALOGS FOR TREATING AND PREVENTING CANCER AND OTHER DISEASES

(71) Applicant: Aphios Corporation, Woburn, MA (US)

(72) Inventor: Trevor P. Castor, Arlington, MA (US)

(73) Assignee: Aphios Corporation, Woburn, MA (US)

( * ) Notice: Subject to any disclaimer, the term of this patent is extended or adjusted under 35 U.S.C. 154(b) by 0 days.

(21) Appl. No.: 15/064,389

(22) Filed: Mar. 8, 2016

(65) Prior Publication Data

US 2016/0184329 A1 Jun. 30, 2016

Related U.S. Application Data

(63) Continuation of application No. 14/329,923, filed on Jul. 12, 2014, now abandoned.

(60) Provisional application No. 61/845,980, filed on Jul. 13, 2013.

(51) Int. Cl.
| | | |
|---|---|---|
| *A61K 9/00* | (2006.01) | |
| *A61K 31/593* | (2006.01) | |
| *A61K 9/127* | (2006.01) | |
| *A61K 9/48* | (2006.01) | |
| *A61K 9/51* | (2006.01) | |

(52) U.S. Cl.
CPC .......... *A61K 31/593* (2013.01); *A61K 9/0019* (2013.01); *A61K 9/127* (2013.01); *A61K 9/4858* (2013.01); *A61K 9/4866* (2013.01); *A61K 9/4875* (2013.01); *A61K 9/5153* (2013.01)

(58) Field of Classification Search
USPC ........................................................ 424/450
See application file for complete search history.

(56) References Cited

U.S. PATENT DOCUMENTS

| | | | | |
|---|---|---|---|---|
| 3,993,754 A | * | 11/1976 | Rahman | A61K 38/04 424/450 |
| 4,737,323 A | * | 4/1988 | Martin | A61K 9/1277 210/500.23 |
| 2005/0059641 A1 | * | 3/2005 | Ray | A61K 31/59 514/167 |
| 2006/0177374 A1 | * | 8/2006 | Curd | A61K 9/4858 424/1.11 |

FOREIGN PATENT DOCUMENTS

WO    WO 96-00074    *    1/1996

OTHER PUBLICATIONS

Swamy, 1996, Affinity labeling of rat serum vitamin D binding protein, Arch Biochem Biophys, 333(1), 139-144.*
Garland et al. (1989) "Serum 25-hydroxyvitamin D and colon cancer: eight-year prospective study," Lancet. 2(8673):1176-1178.

* cited by examiner

*Primary Examiner* — Nannette Holloman
(74) *Attorney, Agent, or Firm* — McCarter & English, LLP; Elizabeth A. Hanley; Mei Bai

(57) ABSTRACT

This invention is for formulations of analogs of the non-toxic and inert Vitamin D3, its non-toxic and mostly inert pre-hormone and its toxic and biologically active hormone, and for using these formulations for preventing and treating certain cancers such as breast, prostate, ovarian, kidney, renal and other cancers, Vitamin D deficiency, autoimmune disease such as Multiple Sclerosis, hypertension, osteoporosis, bone diseases, rickets, psoriasis and infectious diseases. This invention also discloses compositions of the analogs of the non-toxic and inert Vitamin D3 and the non-toxic and mostly inert Vitamin D3 pre-hormone.

4 Claims, 35 Drawing Sheets

FORMULATIONS AND COMPOSITIONS OF VITAMIN D ANALOGS FOR TREATING AND PREVENTING CANCER AND OTHER DISEASES

PRIORITY

This application claims priority to U.S. provisional application Ser. No. 61/845,980 filed Jul. 29, 2013, and is a continuation of U.S. non-provisional application Ser. No. 14/329,923 filed Jul. 12, 2014 each of which is incorporated by reference herein.

GOVERNMENT SUPPORT

Research leading to this invention was in part funded by the National Cancer Institute, National Institutes of Health, Bethesda, Md., USA.

FIELD OF THE INVENTION

This invention relates to formulations and compositions of Vitamin D analogs for the prevention and treatment of cancers and other diseases to minimize the toxic side-effects of the Vitamin D hormone while improving therapeutic index. The formulation methods feature supercritical, critical and near-critical fluids with and without polar cosolvents. This invention also discloses compositions of the analogs of the non-toxic and inert Vitamin D3 and the non-toxic and mostly inert Vitamin D3 pre-hormone.

BACKGROUND OF THE INVENTION

Vitamin D is the general name for a collection of natural sterol-like substances including vitamin $D_2$ and $D_3$. As shown in FIG. 1, Vitamin $D_3$ is synthesized in the skin from 7-dehydrocholesterol, a cholesterol breakdown product, via photochemical reactions using ultraviolet (UV) radiation from sunlight. The inert vitamin $D_3$ is first converted to a largely inert intermediate by the liver to 25-HydroxyVitamin $D_3$ (25-OH-$D_3$) and then converted by the kidney to the bioactive hormone 1-25-DihydoxyVitamin $D_3$ (1,25(OH)$_2D_3$) (FIG. 1). The bioactive vitamin D hormone, 1,25(OH)$_2D_3$, mediates its action by binding to vitamin D receptor (VDR) that is principally located in the nuclei of the target cell.

Vitamin D is a natural molecule that is biosynthesized by the interaction of sunlight with 7-dehydrocholesterol in the epidermis. 1,25-dihydroxyvitamin $D_3$ (1,25(OH)$_2D_3$ named calcitriol), the dihydroxylated metabolite of vitamin $D_3$ is an essential nutrient for skeletal health. Calcitriol has profound effects on the growth and maturation of normal and malignant cells. Several epidemiological studies have demonstrated that people who live in higher latitudes are at higher risk of developing and dying of many cancers, including prostate cancer. It has also been demonstrated that there is an inverse relationship between latitude, sun-exposure and cutaneous synthesis of vitamin D (20). In 1989, Garland et al. carried out an eight-year prospective study among 26,520 healthy adults to demonstrate that if the initial level of serum of calcifediol [25-hydroxyvitamin $D_3$ (25-OH-$D_3$)], the mono-hydroxylated pre-hormonal form of calcitriol is at least 20 ng/ml, there is a 50% reduced risk of developing colon cancer. Since this observation other investigators have confirmed latitudinal impact and vitamin D intake on reducing risk of various cancers, including breast, prostate, renal and ovary. Vitamin D deficiency has also been correlated with autoimmune disease such as Multiple Sclerosis, hypertension, osteoporosis, bone diseases, rickets, psoriasis and infectious diseases.

Prostate cancer (PCA) is the most prevalent cancer among men; and the second leading cause of cancer death among men in the US. More than 500,000 PCA cases are diagnosed each year, 1 in 6 American males will develop PCA and 30,000 die each year in the US. Current clinical interventions for PCA include surgical removal of prostate and radiation therapy, with adverse side effects such as impotence, incontinence and alopecia. The mainstay of hormone-sensitive prostate cancer (HSPCA) chemotherapy is androgen-deprivation. After 9 to 30 months, HSPCA usually becomes insensitive to hormonal therapy and rapidly leads to HRPCA for which there are few interventions except for Sanofi-Aventis' Taxotere® (docetaxel) that has problems of toxicity and other adverse side-effects. New drugs have been recently approved for castration-resistant, docetaxel-refractory prostate cancers that extend life by 4.8 months.

Numerous studies have registered strong promise of calcitriol as a therapeutic agent for prostate and other cancers. However, its clinical use has been limited by risk of toxicity related to hypercalcemia, hypercalciuria, and significant loss of body weight. Attempts to address the toxicity-issue have taken two paths. In the first, combinations of calcitriol with standard chemotherapeutic agents are being investigated to harness synergy between these compounds. For example, clinical and animal studies have been carried out demonstrate that toxic effects of calcitriol can be mitigated by a combination with dexamethasone or paclitaxel.

Several attempts have been made to develop less/non-toxic analogs of calcitriol with potent antiproliferative activities as potential therapeutic agents. A Phase II clinical trial evaluated Seocalcitol (EB-1089), a side-chain analog of the active vitamin D hormone, in patients with inoperable pancreatic cancer. No objective responses (anti-tumor) activity was observed; the most frequent toxicity was dose-dependent hypercalcemia with most patients tolerating a dose of 10-15 μg/day in chronic administration.

The nuclear vitamin D receptor (VDR) plays a central role in the cell signaling process leading to anti-proliferation, and in some cases apoptosis of cancer cells. In this respect calcitriol is very similar to other steroidal and non-steroidal hormones such as estrogen, androgens, retinoids, glucocorticoids etc. Furthermore, VDR has high structural homology with nuclear receptors of other hormones. It is well established that cellular regulation by calcitriol and its analogs are initiated by highly specific binding to VDR, which is translated into pro-differentiation and concomitant antiproliferation of cells. Most human prostate cancer cells contain VDR; and numerous studies have shown that several prostate cancer cells respond to calcitriol. These findings strongly support the use of vitamin D-based agents for first line therapy and/or second line therapy when androgen deprivation fails.

However, cancer-therapy with calcitriol is limited by its rapid catabolic degradation by CYP-hydroxylases, which reduces its potency. As a result high doses of calcitriol are required clinically to harness its beneficial property; but such pharmacological doses cause toxicity. A way of circumventing this problem will be to covalently attach calcitriol into the ligand-binding pocket of VDR as shown in FIG. 2, so that (i) calcitriol is prevented from interacting with catabolic enzymes; and (ii) VDR-mediated transcriptional process could be set in motion since the ligand is inside the ligand-binding pocket of VDR leading to conformational changes required for the transcriptional process.

During the past decade hundreds of vitamin D analogs have been synthesized with the goal of obtaining a better antitumor/toxicity ratio and tumor-specific effect. Although a few of these analogs have successfully completed preclinical studies for several cancers; and at least one analog has recently failed Phase II clinical trials for pancreatic carcinomas, the majority of these compounds have been proved to be of limited therapeutic value due to toxicity. As a result new strategies for developing such analogs are required.

Aspects of the present invention employ materials known as supercritical, critical or near-critical fluids. A material becomes a critical fluid at conditions which equal its critical temperature and critical pressure. A material becomes a supercritical fluid at conditions which equal or exceed both its critical temperature and critical pressure. The parameters of critical temperature and critical pressure are intrinsic thermodynamic properties of all sufficiently stable pure compounds and mixtures. Carbon dioxide, for example, becomes a supercritical fluid at conditions which equal or exceed its critical temperature of 31.1° C. and its critical pressure of 72.8 atm (1,070 psig). In the supercritical fluid region, normally gaseous substances such as carbon dioxide become dense phase fluids which have been observed to exhibit greatly enhanced solvating power. At a pressure of 3,000 psig (204 atm) and a temperature of 40° C., carbon dioxide has a density of approximately 0.8 g/cc and behaves much like a nonpolar organic solvent, having a dipole moment of zero Debyes.

A supercritical fluid displays a wide spectrum of solvation power as its density is strongly dependent upon temperature and pressure. Temperature changes of tens of degrees or pressure changes by tens of atmospheres can change a compound solubility in a supercritical fluid by an order of magnitude or more. This feature allows for the fine-tuning of solvation power and the fractionation of mixed solutes. The selectivity of nonpolar supercritical fluid solvents can also be enhanced by addition of compounds known as modifiers (also referred to as entrainers or cosolvents). These modifiers are typically somewhat polar organic solvents such as acetone, ethanol, methanol, methylene chloride or ethyl acetate. Varying the proportion of modifier allows wide latitude in the variation of solvent power.

In addition to their unique solubilization characteristics, supercritical fluids possess other physicochemical properties which add to their attractiveness as solvents. They can exhibit liquid-like density yet still retain gas-like properties of high diffusivity and low viscosity. The latter increases mass transfer rates, significantly reducing processing times. Additionally, the ultra-low surface tension of supercritical fluids allows facile penetration into microporous materials, increasing extraction efficiency and overall yields.

A material at conditions that border its supercritical state will have properties that are similar to those of the substance in the supercritical state. These so-called "near-critical" fluids are also useful for the practice of this invention. For the purposes of this invention, a near-critical fluid is defined as a fluid which is (a) at a temperature between its critical temperature ($T_c$) and 75% of its critical temperature and at a pressure at least 75% of its critical pressure, or (b) at a pressure between its critical pressure ($P_c$) and 75% of its critical pressure and at a temperature at least 75% of its critical temperature. In this definition, pressure and temperature are defined on absolute scales, e.g., Kelvin and psia. To simplify the terminology, materials which are utilized under conditions which are supercritical, near-critical, or exactly at their critical point with or without polar co-solvents such as ethanol will jointly be referred to as "SuperFluids™" or referred to as "SFS." SuperFluids™ were used for the nanoencapsulation of the Vitamin D analog in the protective lipid layer of phospholipid nanosomes.

SUMMARY OF THE INVENTION

Embodiments of the present invention are directed to the composition, formulation and use of Vitamin D analogs, that bind tightly into the Vitamin D receptor, and can be used therapeutically at lower doses than their Vitamin D counterparts, and are such less toxic than their Vitamin D counterparts.

AMPI-109 is a bromoacetate derivative ($1\alpha,25$-dihydroxyvitamin $D_3$-3-bromoacetate [$1,25(OH)_2D_3$-3-BE]) the active Vitamin $D_3$ hormone (FIG. 3).

AMPI-105 is a bromoacetate derivative (25-hydroxyvitamin $D_3$-3-bromoacetate [25-OH-$D_3$-3-BE]) of the non-toxic pre-hormonal form of Vitamin $D_3$ (FIG. 4).

AMPI-106 is the epoxide derivative (25-hydroxyvitamin $D_3$-3-epoxide [25-OH-$D_3$-3-EPO]) of the non-toxic pre-hormonal form of Vitamin $D_3$ (FIG. 5).

AMPI-107 is the epoxide derivative ($D_3$-3-epoxide [$D_3$-3-EPO]) of the non-toxic and inert Vitamin $D_3$ (FIG. 6).

Embodiments of the present invention are directed to formulations of these Vitamin D analogs to prolong circulation time while reducing systemic toxicity and enhancing therapeutic index.

In order to prolong circulation time while reducing systemic toxicity and enhancing therapeutic index, the less toxic Vitamin D analogs are nanoencapsulated within the lipid bilayer of phospholipid nanosomes. Nanoencapsulation also enhances serum stability. Phospholipid nanosomes will also protect the ester bond from hydrolysis increasing the half-life of Vitamin D analogs.

Nanoencapsulation allows Vitamin D analogs to kinetically engage VDR to increase the half-life of calcitriol, thereby potentially increasing its potency with less toxicity.

Using SCCNC fluids, AMPI-109 was encapsulated into phospholipid nanosomes (APH-0701), which were ~100 to 200 nm in size, had high encapsulation efficiencies around 75%, with passive in vitro release rates of ~3 days.

APH-0701 was found to be stable in human serum and mouse liver homogenates.

Both AMPI-109 and APH-0701 were effective in reducing tumor-size in mouse xenograft models of DU-145 (androgen-insensitive) tumors. Compared to a nanosomal vehicle control, AMPI-109 and APH-0701 reduced tumor size approximately 37% and 49%.

Gross body-weights of AMPI-109 and APH-0701-treated animals were not significantly different from control animals, indicating lack of gross toxicity.

Collectively these results demonstrated that AMPI-109 and APH-0701 have a strong translational potential as a therapeutic agent in androgen-insensitive prostate cancer.

DETAILED DESCRIPTION OF PREFERRED EMBODIMENTS

AMPI-109 (1α,25-dihydroxyvitamin $D_3$-3-bromoacetate [1,25(OH)$_2$D$_2$-3-BE])

Figure 1:
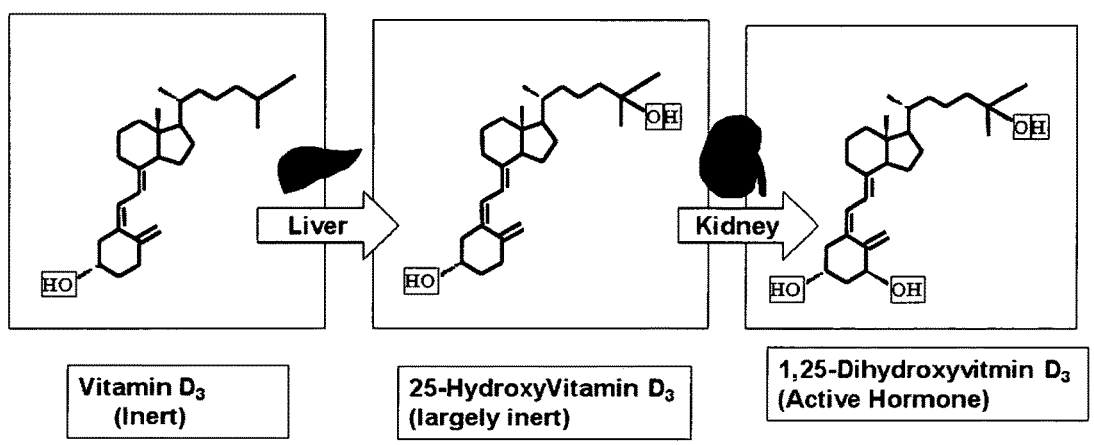
FIG. 1 depicts Biosynthesis of inert Vitamin $D_3$ in skin, conversion into the largely inert pre-hormone in the liver and the highly bioactive hormone in the kidney.
Figure 2:
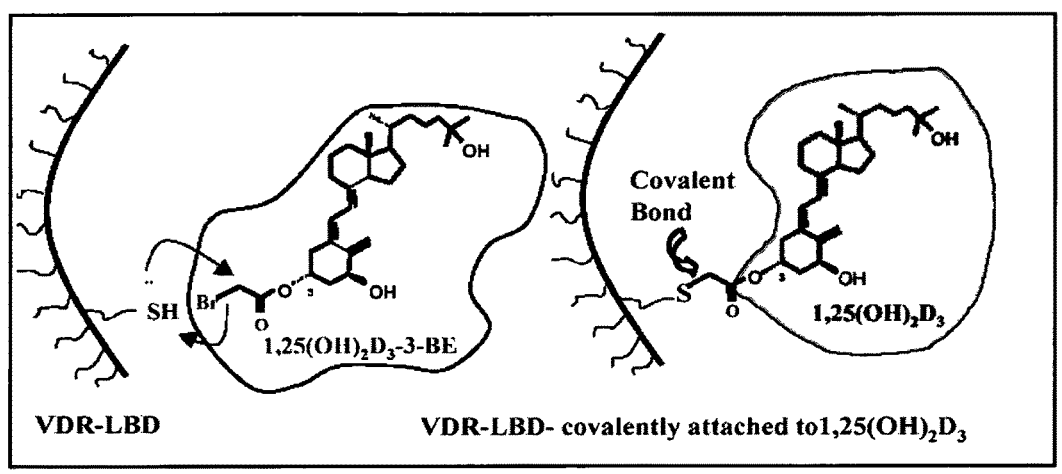
FIG. 2 depicts Cross-linking of $1,25(OH)_2D_3$-3-BE (AMPI-109) into the VDR-ligand binding pocket via $Cys_{288}$.

The Vitamin D analog 1α,25-dihydroxyvitamin $D_3$-3-bromoacetate [1,25(OH)$_2$D$_3$-3-BE]), AMPI-109, is a derivative of calcitriol covalently links calcitriol inside the ligand-binding pocket of VDR via a cysteine residue as shown in FIG. 2. We also observed that such a process constitutively activated VDR. Thus, AMPI-109 became a significantly stronger anti-proliferative agent than calcitriol on a mole-per-mole basis in LNCaP, PC-3 and DU-145 prostate cancer cells (6.5 more times for DU-145 in hormone refractory prostate cancer (HRPCA) animal models). AMPI-109 is a significantly stronger antiproliferative agent than EB-1089, a side-chain analog of calcitriol that underwent clinical trials, in DU-145 cancers. In addition, AMPI-109 induced apoptosis in these cells. Furthermore, in in vivo studies, AMPI-109 produced strong anti prostate tumor effect without inducing significant toxicity in athymic mice. Therefore, AMPI-109 demonstrates a strong translational potential as a therapeutic agent for prostate cancer.

There may be concerns that AMPI-109 may: (i) behave like protein/DNA alkylating compounds with significant side effects at pharmacological doses; (ii) generate adverse immune responses; and (iii) be prematurely hydrolyzed since it contains an ester bond. Unlike protein/DNA alkylating compounds such as estramustine and lomustine that are non target-specific and produce significant side effects particularly at pharmacological doses, AMPI-109 will interact with specific targets and cross-link to the substrate/ligand-binding sites of enzymes and receptors and thus, will have less side effects. Adverse immune response of the alkylating agents, such as AMPI-109, is difficult to predict. Calcitriol and its analogs are touted as potential drug-candidates for immune-deficiency diseases, such as Type I diabetes. Therefore, AMPI-109 is expected, if anything to show a positive immune response. Since AMPI-109 contains an ester bond, hydrolysis would produce calcitriol and bromoacetic acid; such a phenomenon might limit bioavailability of the intact molecule. This phenomenon is minimized by nanoencapsulation of the Vitamin D analog in the protective lipid membrane of the nanoparticles. In a cellular proliferation study, the antiproliferative property of AMPI-109 is due solely to its un-hydrolyzed and intact form.

The covalent attachment of calcitriol into the ligand-binding pocket of VDR prevents the catabolism of calcitriol because it will be sitting deep inside the binding pocket, and will be inaccessible to catabolizing CYP enzymes.

DU-145 is a highly aggressive androgen-insensitive human prostate cancer cell line that does not respond well to calcitriol due to increased expression of CYP 24-OHase and rapid catabolism. AMPI-109 shows a strong and dose-dependent antiproliferative effect in DU-145 cells, while calcitriol shows no effect. By decreasing catabolism of calcitriol by first protecting its analog in the lipid layer and then cross-linking it to the ligand-binding pocket of VDR (via AMPI-109), the potency of the hormone is significantly increased. AMPI-109 also modulate messages for human osteocalcin and CYP 24-OHase (genes that are involved in the VDR-mediated mechanism) in keratinocytes similar to calcitriol. The message for 24-OHase is up regulated by calcitriol and AMPI-109 in LNCaP cells, and this message is obliterated by ZK 159222, a calcitriol antagonist. These results strongly indicate that cellular effects of AMPI-109 follow a mechanism similar to that of calcitriol.

Synthesis of AMPI-109

Figure 3:
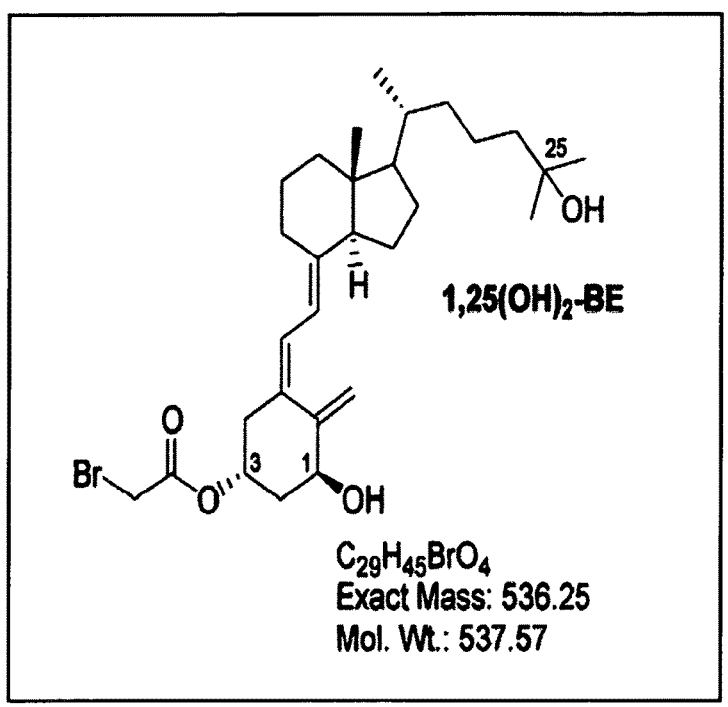
FIG. 3 depicts the bromoacetate derivative ($1\alpha,25$-dihydroxyvitamin $D_3$-3-bromoacetate [$1,25(OH)_2D_3$-3-BE]) of the active Vitamin $D_3$ hormone (AMPI-109).

$1,25(OH)_2D_3$-3-BE (AMPI-109) shown in FIG. 3 was synthesized. The structure of AMPI-109 was confirmed by proton and $^{13}C$ NMR; the molecular weight was established by mass spectral analysis to be 536.25; and the purity determined to be >98.3% at 265 nm by reversed phase HPLC.

Analysis of AMPI-109

Figure 7:
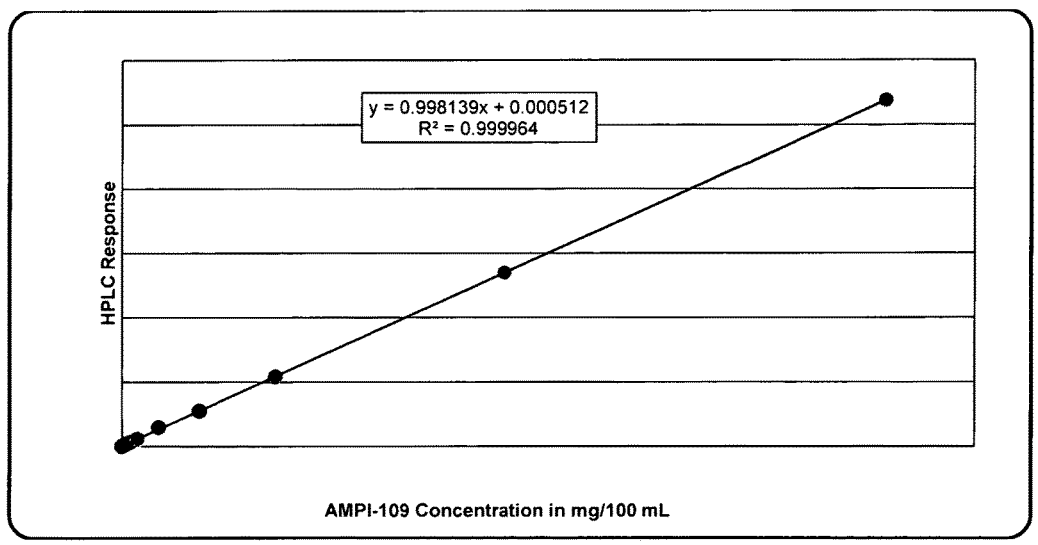
FIG. 7 depicts AMPI-109 Standard Curve.

AMPI-109 and the formulated product were analyzed by HPLC. The HPLC method utilized a Phenomenex Luna C18(2), 100 A, 5 micron, 150×4.6 mm HPLC column (P/No.: OOF-4252-EO; S/No. 425310-16), a mobile phase consisting of 95% acetonitrile: 5% water, a flow rate of 1.0 mL/min, a column temperature of 30° C., an injection volume of 20 μL and a run time of 10 minutes with monitoring at 265 nm. AMPI-109's standard curve is shown in FIG. 7. A system suitability requirement of Plates >4,000 was established for the method. The limit of detection (LOD) was determined to be 0.013 ppm and limit of quantification (LOQ) to be 0.04 ppm. Injection replication was determined to have a root square difference (RSD) of 0.21%.

Formulation of AMPI 109

We utilized the SuperFluids™ critical fluid nanosome (CFN) process for the formation of small, uniform liposomes (nanosomes) for encapsulating AMPI-109. Liposomal preparations are identified as AMPI-109 (L) and APH-0701.

Figure 8:
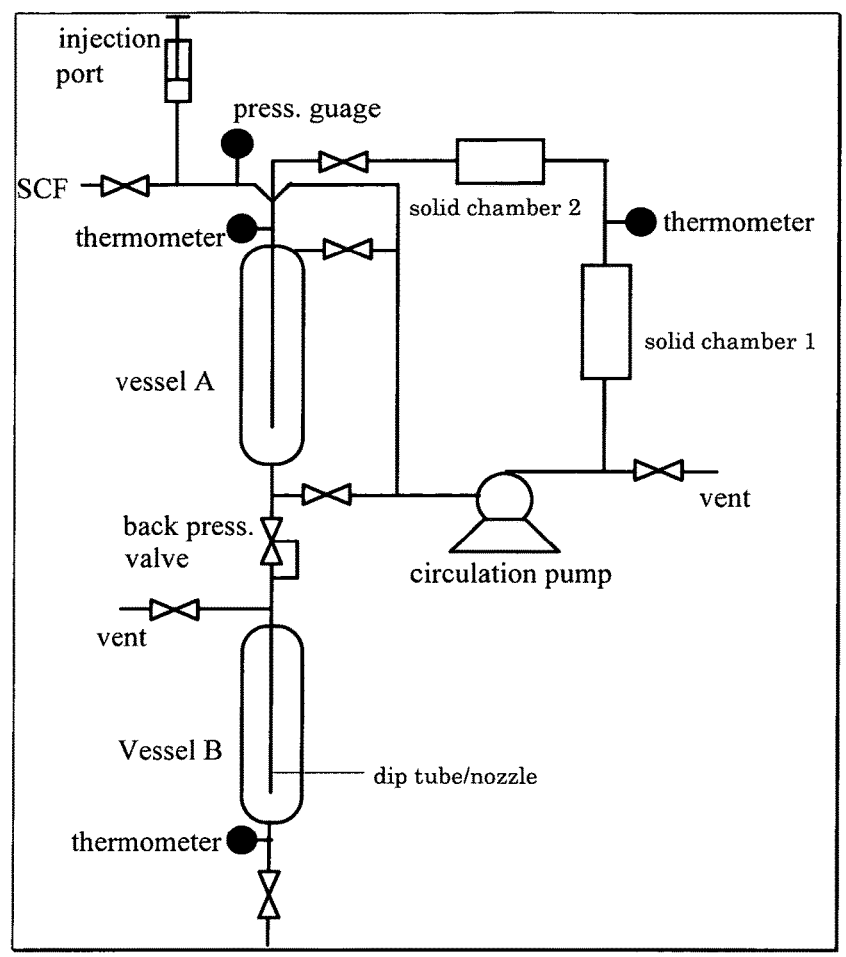
FIG. 8 depicts SFS-CFN Apparatus.

Twenty-seven encapsulation runs were performed in the SFS-CFN apparatus shown schematically as FIG. 8. In a typical SFS-CFN experiment, the solids chamber was charged with dimyristoyl-phosphatidylcholine (DMPC) or phosphatidylcholine (PC) and cholesterol and placed inline within the apparatus. The molar ratio of lipid:cholesterol: drug was designed to be 20:1:1. The system was then pressurized between 2,000 and 3,000 psig with a SFS (Freon 23 or propane) and heated to the desired temperature (40 to 60° C.). The lipids were dissolved into the SFS through circulation of the SFS within the upper high pressure circulation loop in the apparatus for ~60 min, before adding AMPI-109 dissolved in ethanol (EtOH) via an injection port into the high pressure circulation loop. After a specific residence time, the resulting mixture was decompressed via a backpressure regulator (valve) though a dip tube with a nozzle into a decompression chamber (vessel B), which contained a buffer such as a 10% sucrose solution. After decompression through the nozzle, the SuperFluids™ were evaporated off leaving an aqueous solution of nanosomes entrapping the hydrophobic AMPI-109 within the lipid bilayers, forming APH-0701.

Three samples were typically taken: depressurization at constant pressure, depressurization from operating pressure to 400 psig, and depressurization from 400 psig to atmospheric pressure. Most of the AMPI-109 was contained in the second fraction. This fraction was the sterile filtered through a 0.2 μm polycarbonate or a nitroplus cellulosic filter using compressed $N_2$. The filtrates were checked for AMPI-109 content as well as for particle size. In a typical example, after filtration, the sterile samples were dispensed with a sterile, disposable pipette in 5 mL aliquots into sterile 20 mL vials and frozen at −80° C. The samples were then freeze-dried overnight and weighed. Lyophilized samples were then reconstituted in 5 mL DI-$H_2O$, sonicated for 20 seconds three times, and analyzed for particle size and AMPI-109 content.

AMPI-105 and AMPI-106 (25-OH-$D_3$ Analogs)

Figure 4:
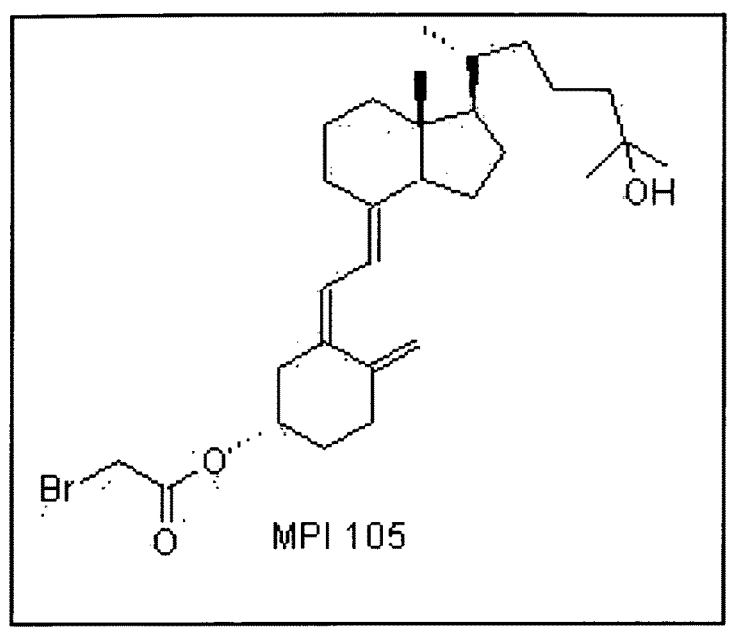
FIG. 4 depicts the bromoacetate derivative (25-hydroxyvitamin $D_3$-3-bromoacetate [25-OH-$D_3$-3-BE]) of the non-toxic pre-hormonal form of Vitamin $D_3$ (AMPI-105).
Figure 5:
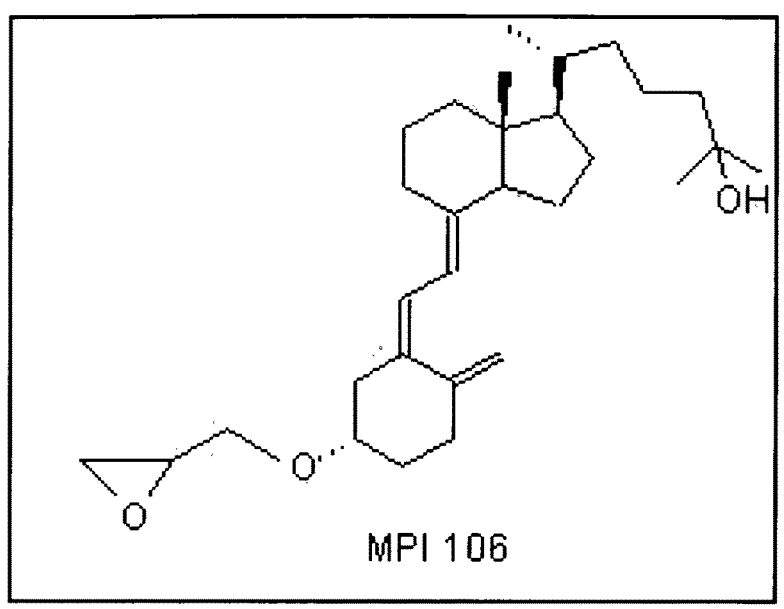
FIG. 5 depicts the epoxide derivative (25-hydroxyvitamin $D_3$-3-epoxide [25-OH-$D_3$-3-EPO]) of the non-toxic pre-hormonal form of Vitamin $D_3$ (AMPI-106).

AMPI-105 and AMPI-106 are analogs of 25-HydroxyVitamin $D_3$ (25-OH-$D_3$). AMPI-105 is a bromoacetate derivative (25-hydroxyvitamin $D_3$-3-bromoacetate [25-OH-$D_3$-3-BE]) of the non-toxic pre-hormonal form of Vitamin $D_3$ (FIG. 4). AMPI-106 is the epoxide derivative (25-hydroxyvitamin $D_3$-3-epoxide [25-OH-$D_3$-3-EPO]) of the non-toxic pre-hormonal form of Vitamin $D_3$ (FIG. 5).

AMPI-105 and AMPI-106 are a class of novel, non-toxic VDR affinity-binding analogs of 25-OH-$D_3$. By covalently attaching (alkylating) 25-OH-$D_3$, a non-toxic and biologically inert pre-hormonal form of $1,25(OH)_2D_3$, to the hormone-binding pocket of VDR, 25-OH-$D_3$ was to converted into a transcriptionally active form. This makes 25-OH-$D_3$ biologically active. Furthermore, it translates the non-toxic nature of 25-OH-$D_3$ into its VDR-alkylating analog. Thereby, the 25-OH-$D_3$ analogs now have the anti-cancer property of a '$1,25(OH)_2D_3$-like molecule' without systemic toxicity.

As shown in the examples, the two (2) VDR-alkylating analogs of 25-OH-$D_3$ (AMPI-105 and AMPI-106) possess strong anti-tumor activity in a mouse prostate tumor xenograft model.

AMPI-107 (Vitamin $D_3$ Analog)

Figure 6:
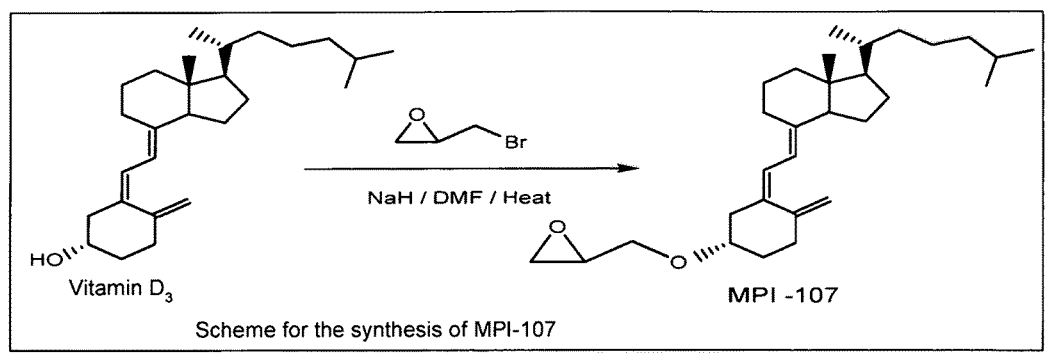
FIG. 6 depicts the epoxide derivative (Vitamin $D_3$-3-epoxide [$D_3$-3-EPO]) of the non-toxic and inert Vitamin $D_3$ (AMPI-107).

AMPI-107 is an epoxide analog of Vitamin $D_3$ (FIG. 6). Vitamin $D_3$ is normally considered to be biologically inert.

As shown in the examples, the very strong anti-growth activity of AMPI-107, a vitamin $D_3$ derivative, even at 10-times higher dose level is highly unexpected and significant.

EXAMPLES

Example 1: APH-0701 Nanosomes Characterization

Experiment APH-0701-27 was conducted with SFS propane at 3,000 psig and 60° C. Three depressurization fractions were collected in 10% sucrose. The first was obtained by displacement under constant pressure, the second by depressurization from 3,000 psig to ~400 psig and the third by depressurization from ~400 psi to 0 psig. These were APH-0701-27-01, APH-0701-27-02 and APH-0701-27-03 respectively. The results of the analysis of APH-0701-27 are summarized in Table 1.

TABLE 1

AMPI-109 Content and Size of APH-0701-27

| APH-0701-27 Fractions | Amount of AMPI-109 (mg) | Size (nm) | Recovered (%) |
|---|---|---|---|
| APH-0701-27-01 | 0.013 | 4740 | 1.5 |
| APH-0701-27-02 | 0.745 | 197 | 88.5 |
| APH-0701-27-03 | 0.084 | — | 10.0 |
| Total | 0.842 | — | 100.0 |

Figure 9:
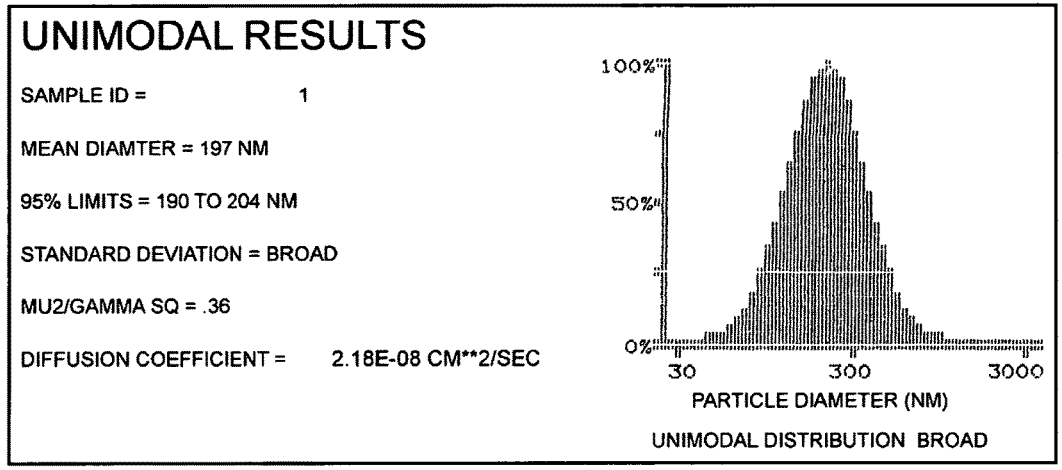
FIG. 9 depicts Particle Size Analysis of APH-0701-27-02 Nanosomes.
Figure 10:
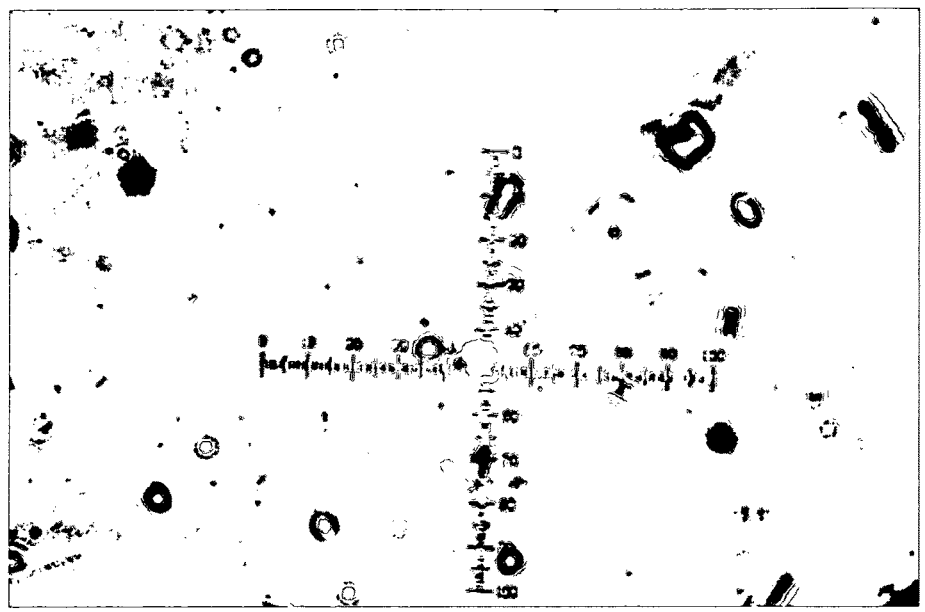
FIG. 10 depicts Photomicrograph of APH-0701-27-02.

The particle size of APH-0701-27-02, which contained 88.5% of AMPI-109, was determined to be 197 nm using a Coulter 4MD particle size analyzer (FIG. 9). This particle size was confirmed by photomicrography at a magnification of 1,000× (FIG. 10).

Example 2: Size Exclusion Chromatography

Figure 11:
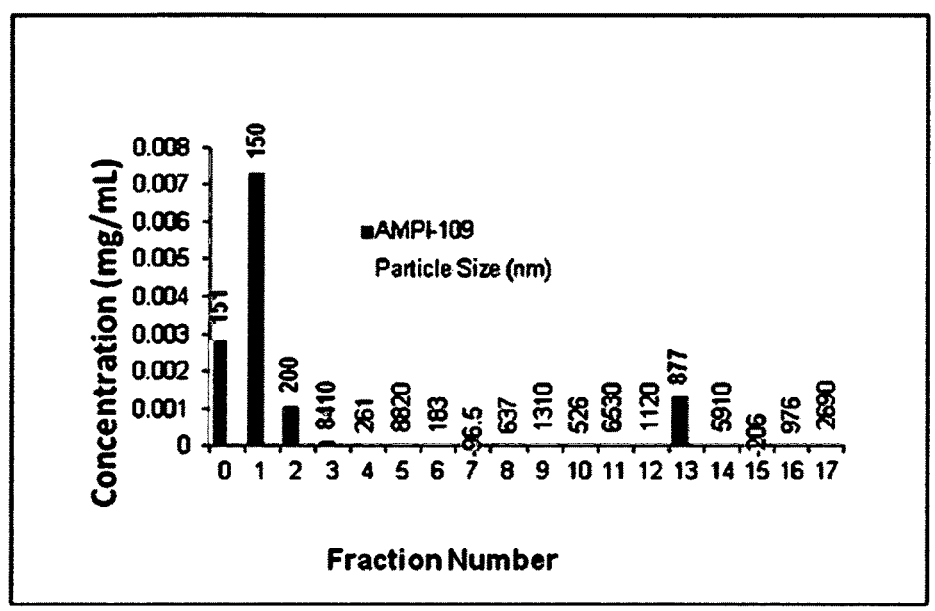
FIG. 11 depicts SEC Separation of APH-0701-27-02.

In order to determine the extent of encapsulation of AMPI-109, a size exclusion separation of VDD-27-02 was conducted on Sephadex LH-20. In this size exclusion separation, phospholipid nanosomes should elute with the void volume with smaller molecules retained onto the column and eluted after solvent wash. The results, shown in FIG. 11, indicate that the majority (~90%) of AMPI-109 elutes with the phospholipid nanosomes in the first three fractions with particle sizes of 151 nm, 150 nm and 200 nm, around those originally measured.

Example 3: In Vitro Release of AMPI-109 from Nanosomes

Figure 12:
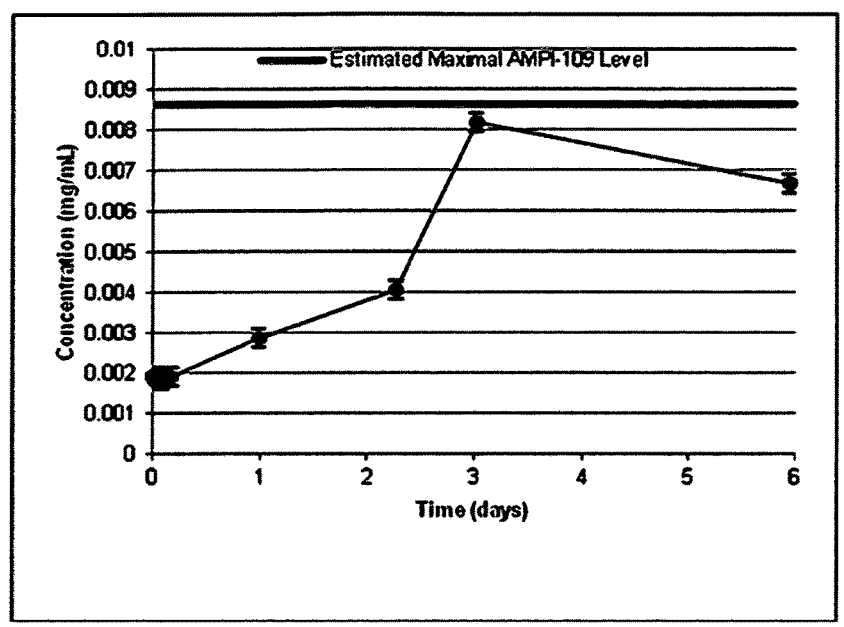
FIG. 12 depicts Release of AMPI-109 from APH-0701-27-02.

Release studies of VDD-27-02 into 10% Tween 80 solution in FIG. 12 indicate that AMPI-109 is releasing from nanosomes slowly over time until almost all has either diffused out or the nanosomes have broken apart. Maximum release is observed after 3 days, after which time, AMPI-109 is either precipitating or degrading.

Example 4: Antiproliferative and Cytotoxic Activity of APH-0701 and AMPI-109 in Prostate Cancer Cells by $^3$H-Thymidine Incorporation Assay The activities of AMPI-109 in nanosomes (APH-0701) vs. naked AMPI-109 were measured in androgen-sensitive LNCaP prostate cancer cells. Anti-proliferative activity was compared with nanosomal preparation of AMPI-109 (APH-0701) versus naked AMPI-109. Antiproliferative activities in these cells were measured by $^3$H-thymidine incorporation assay.

$^3$H-Thymidine-Incorporation Assay:

In a typical assay cells were grown to 50-60% confluence in 24-well plates in respective media containing 5% FBS, and serum starved for 20 hours, followed by treatment with various agents (in 0.1% ethanolic solution) or ethanol (vehicle) in serum-containing medium for 16 hours. After the treatment media was removed from the wells and replaced with media containing $^3$H-thymidine (Sigma, 0.1 µCi) per well, and the cells were incubated for 3 hours at 37° C. After this period media was removed by aspiration and the cells were washed thoroughly (3×0.5 ml) with PBS. Ice-cold 5% perchloric acid solution (0.5 ml) was added to each well and the cells were incubated on ice for 20 minutes. After this incubation, perchloric acid was removed by aspiration, replaced with 0.5 ml of fresh perchloric acid solution and the cells were incubated at 70° C. for 20 minutes. Solution from each well was mixed with scintillation fluid and counted in a liquid scintillation counter. There were eight (8) wells per sample; statistics was carried out by Student's t test.

Figure 13:
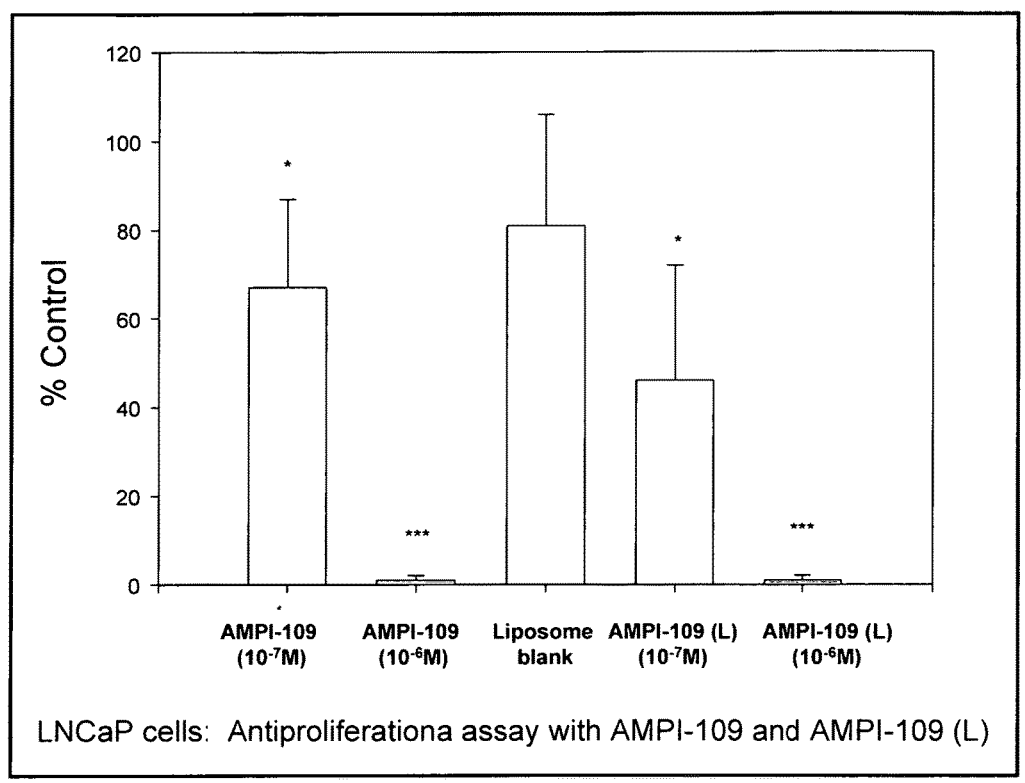
FIG. 13 depicts LNCaP cells: Antiproliferation assay with AMPI-109 and APH-0701.

AMPI-109, both in naked and nanosomal forms has strong antiproliferative effect in LNCaP prostate cancer cells (FIG. 13). Both AMPI-109 and APH-0701 [aka AMPI-109 (L)] almost completely inhibited the growth of LNCaP cells.

At $10^{-7}$M dose level of APH-0701 has significantly stronger effect than an equivalent amount of AMPI-109. Encapsulation of AMPI-109 prevents catabolic degradation of naked AMPI-109; and as a result APH-0701 has a stronger biological/cellular effect, as we have observed with LNCaP prostate cancer cells.

Example 5: Antiproliferative and Cytotoxic Activity of AMPI-109 vs 1,25(OH)$_2$D$_3$ (Calcitriol) in Normal Kidney and Kidney Cancer Cells by $^3$H-Thymidine Incorporation Assay The antiproliferative activities of AMPI-109 and Calcitriol (1,25(OH)$_2$D$_3$) are shown in FIG. 14 for normal kidney cells and in FIG. 15 for RCC 54 kidney cancer cells.

Figure 14:
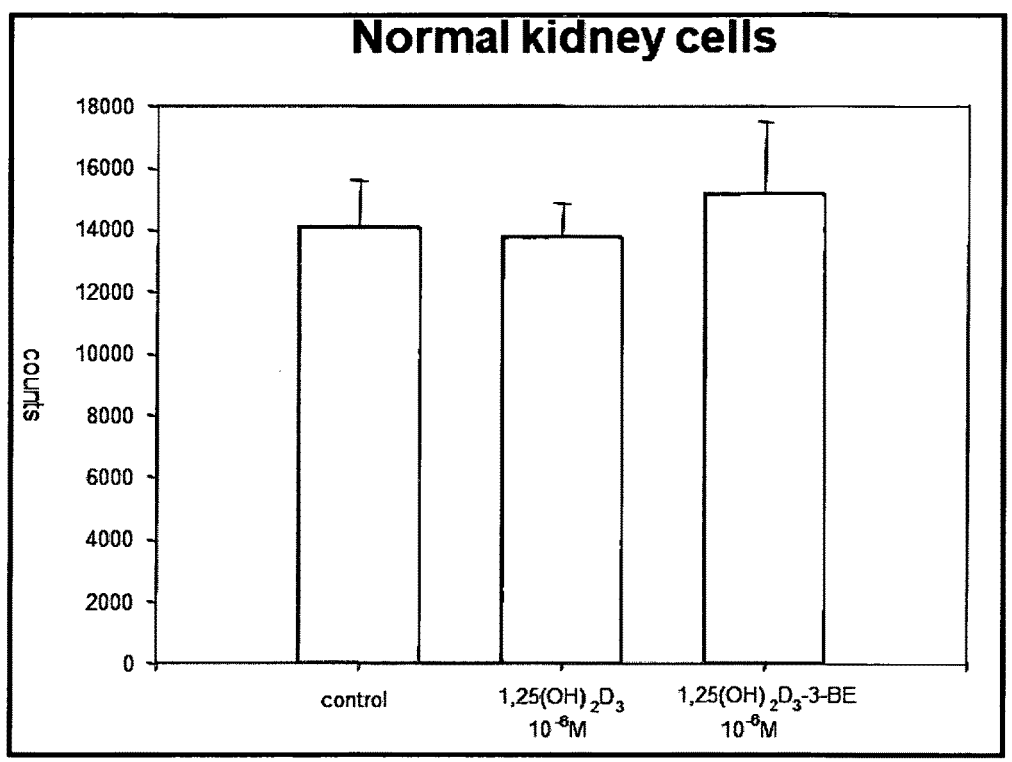
FIG. 14 depicts antiproliferative and cytotoxic activity of AMPI-109 (Vitamin $D_3$-3-epoxide [$D_3$-3-EPO]) vs Calcitriol (1,25(OH)$_2$D$_3$) in normal kidney cells by $^3$H-thymidine incorporation assay.

At $10^{-6}$M, neither Calcitriol nor AMPI-109 had any statistically different impact on normal kidney cells than the control (FIG. 14).

Figure 15:
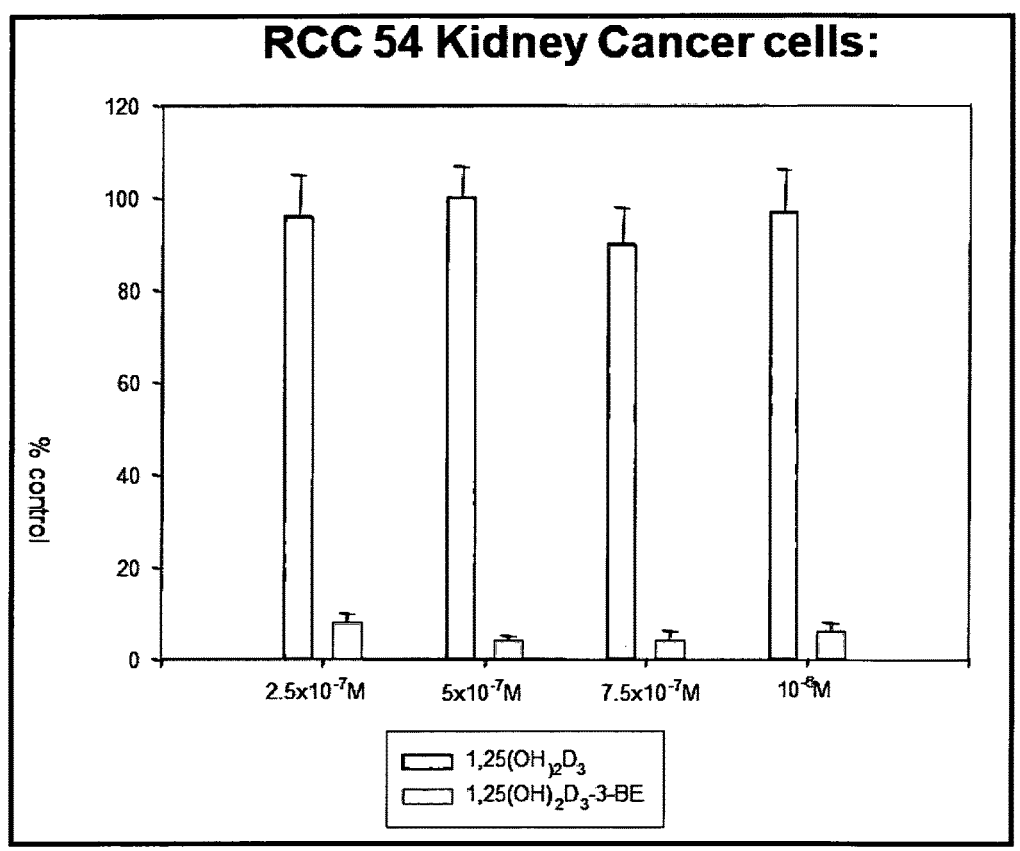
FIG. 15 depicts antiproliferative and cytotoxic activity of AMPI-109 (Vitamin $D_3$-3-epoxide [$D_3$-3-EPO]) vs Calcitriol (1,25(OH)$_2$D$_3$) in kidney cancer cells by $^3$H-thymidine incorporation assay.

Surprisingly, at doses ranging from $7.5\times10^{-7}$ to $10^{-6}$M, Calcitriol did not have any statistically different impact on RCC 54 kidney cancer cells over control whereas AMPI-109 had a >95% impact on the reduction of proliferation of RCC 54 kidney cancer cells (FIG. 15).

The APH-0701 nanosomal formulation of AMPI-109 will have a similar impact to that shown in Example 4 of reducing its toxicity to normal kidney cells and increasing its efficacy on kidney cancer cells.

Example 6: Effect of 1,25(OH)$_2$D$_3$-3-BE (AMPI-109) Vs 1,25(OH)$_2$D$_3$ (Calcitriol) and EB-1089 on the Growth of Androgen-Insensitive Human Prostate Cancer Du-145 Cells DU-145 is a highly aggressive androgen-insensitive human prostate cancer cell line that does not respond well to calcitriol due to increased expression of CYP 24-OHase and subsequent rapid catabolism. We hypothesized that covalent attachment of calcitriol (via AMPI-109) into the ligand-binding pocket of VDR might make it inaccessible to catabolic enzymes; and hence restore its activity. To prove this point we treated DU-145 cells (grown to approximately 60% confluence) in DMEM media containing 5% FBS with $2.5\times10^{-7}$M, $5.0\times10^{-7}$M, $7.5\times10^{-7}$M and $10.0\times10^{-7}$M ($10^{-6}$M) of AMPI-109, calcitriol or ethanol for 20 hours followed by antiproliferation analysis by $^3$H-thymidine-incorporation assay.

Figure 16:
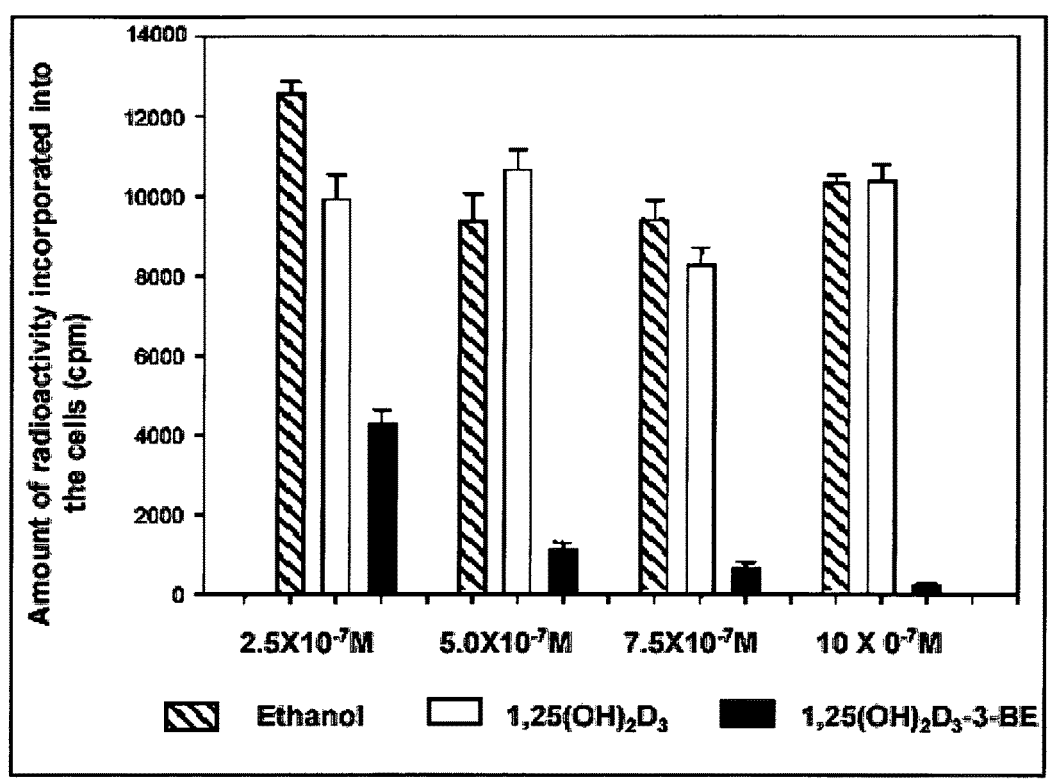
FIG. 16 depicts DU-145 cells treated with various doses of Calcitriol or AMPI-109 or ethanol (vehicle) for 20 hours followed by $^3$H-thymidine incorporation assay.
Figure 17:
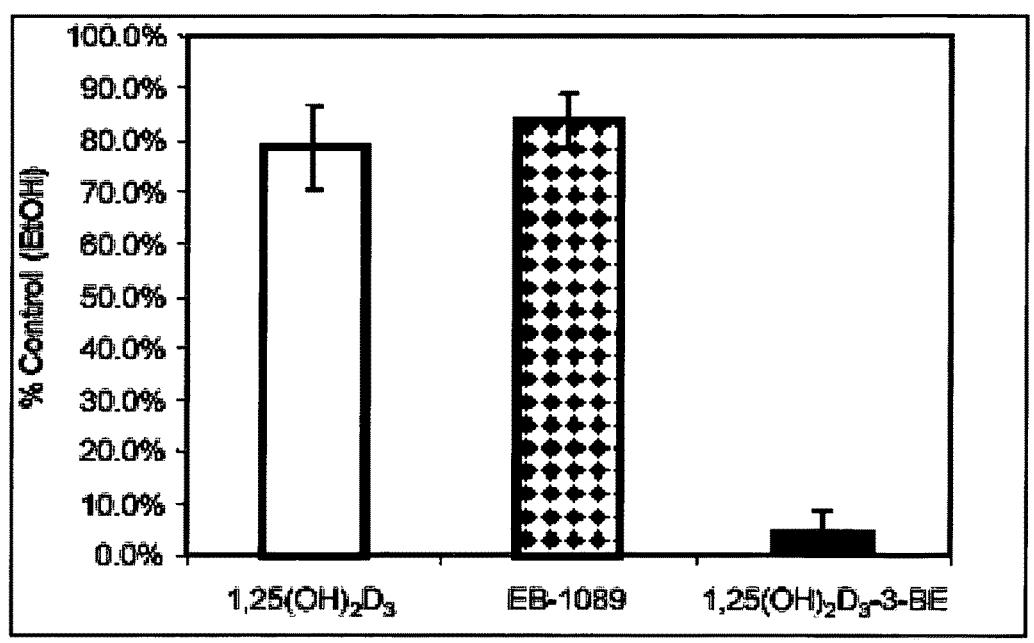
FIG. 17 depicts Effect of AMPI-109, Calcitriol or EB-1089 on the growth of DU-145 cells.

The data in FIG. 16 demonstrates that AMPI-109 showed a dose-dependent antiproliferative effect in DU-145 cells with maximum effect at $10^{-6}$M dose, while calcitriol showed no effect. In a separate experiment (data shown in FIG. 17), we treated DU-145 cells with $10^{-6}$M of calcitriol, AMPI-109 or EB-1089 (a non-calcemic analog of calcitriol). AMPI-109 showed a strong anti-proliferative effect at $0^{-6}$M, but both calcitriol and EB-1089 failed to produce any discernible anti-proliferative effect.

Example 7: Serum-Stability Study of AMPI-109 and APH-0701

One ml of pooled human serum was incubated at 37° C. for 60 minutes with 10 g of AMPI-109 or an equivalent amount of APH-0701 followed by multiple (5 times) extraction with 0.5 ml of ethyl acetate. The organic layer was dried in a stream of nitrogen and the residue was analyzed by HPLC (5% $H_2O$— 95% methanol 1.5 ml/min, 265 nm detection, Agilent C18 column).

Organic extracts of both AMPI-109 and APH-0701 produced a peak at 6.68 min which corresponds to the peak of a standard sample of AMPI-09.

These results demonstrate that APH-0701 is stable in human serum.

Example 8: Stability Study of AMPI-109 and APH-0701 in Liver Homogenate

Pieces of liver, obtained from normal mice were minced and homogenized in phosphated saline with a polytron. One mL of the homogenate was incubated at 37° C. for 60 minutes with 10 µg of AMPI-109 or an equivalent amount of APH-0701 followed by multiple (5 times) extraction with 0.5 mL of ethyl acetate. The organic layer was dried in a stream of nitrogen and the residue was analyzed by HPLC (as above). Organic extracts of both AMPI-109 and APH-0701 produced a peak at 6.1-6.3 min which corresponds to the peak of a standard sample of AMPI-109.

These results demonstrate that APH-0701 is stable in a mouse liver homogenate.

Example 9: Maximum Tolerated Dose (MTD) of AMPI-109 and APH-0701 in SCID Mice DU-145 prostate cancer cells (ATCC, Manassas, Va.) were grown in culture, and then approximately 5 million cells/animal was injected under the skin in the flank area of SCID mice (Charles River). Tumors grew in 2-3 weeks, and when they reached a size of approximately 1 $cm^3$, they were injected with 0.1, 0.5 and 1 µg/kg dose of AMPI-109 (in 5% dimethylacetate in sesame oil) intraperitoneally. Dosing levels were limited by concentrations and volumes. Each group had six mice. Dosing was carried out every third day and weight of each mouse was recorded. All mice in the 1 µg/Kg dose died after three dosing.

Based on dosing, the relative MTD of AMPI-109 is estimated to be ≤3 µg/Kg.

Twenty (20) male nu/nu mice, 6 weeks old (Charles River Laboratories, Wilmington, Mass.) were grouped in five (5) animals each and injected (i.p.) with either vehicle (blank liposome) or 0.75 µg/kg, 1.0 µg/kg and 1.25 µg/kg of APH-0701, the liposomal preparation of AMPI-109 on every third day. Mice were observed for sign of toxicity including lack of appetite, weight loss, lethargy etc. After seven (7) injections three (3) mice (out of a total of 5) receiving 1.25 µg/kg of APH-0701 died, and the experiment was stopped.

Based on dosing, the relative MTD of APH-0701 is estimated to be >9 µg/Kg.

Thus the maximum tolerated dose of APH-0701, the nanoformulated Vitamin D analog, is at least 300% higher than that of the naked Vitamin D analog, AMPI-109.

Example 10: In Vivo Efficacy of AMPI-109 and Calcitriol in Mouse Xenograft Models of Androgen-Insensitive DU-145 Human Prostate Cancer Cells (I.P.-Administration)

Male, athymic mice (average weight 20 gm) were fed normal rat chow and water ad libitum. They were inoculated with DU 145 cells, grown in culture in their flanks under light anesthesia. When the tumor size grew to approximately 100 $mm^3$ the animals were randomized into groups of ten (10) tumor-bearing animals, and they were given AMPI-109 (0.1 µg/kg), calcitriol (0.5 and 1 µg/kg), and vehicle (5% DMA in sesame oil) by intraperitoneal injection (i.p.) on every third day (when body weights were determined); and one group was left untreated. Treatment started on day 11 and stopped on day 30; and they were left untreated for two (2) additional days when they were sacrificed.

Figure 18:
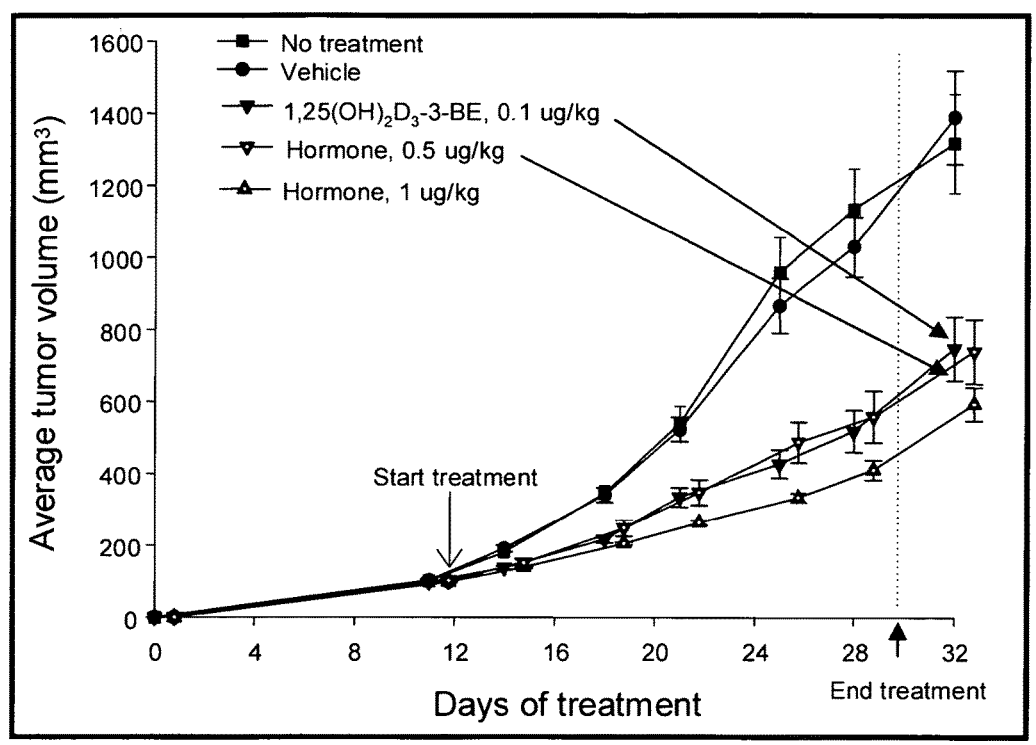
FIG. 18 depicts Effect of 1,25(OH)$_2$D$_3$-3-BE and 1,23 (OH)$_2$D$_3$ (Hormone) (q.o.d.×10, i.p.) on tumor volume in athymic DU-145 mice.

AMPI-109 (0.1 µg/kg) showed a strong anti-tumor effect (solid purple triangle in FIG. 18). Effect of AMPI-109 (0.1 µg/kg) was similar to calcitriol (0.5 µg/kg). AMPI-109 was approximately 5 times stronger in potency than calcitriol in reducing tumor-size. However, molecular weights of calcitriol and AMPI-109 are 416.65 and 537.8 respectively. Therefore, on a molar basis AMPI-109 is approximately 6.5 times more potent than calcitriol. Thus, covalently attaching calcitriol to VDR might increase its potency (by decreasing catabolism).

Figure 19:
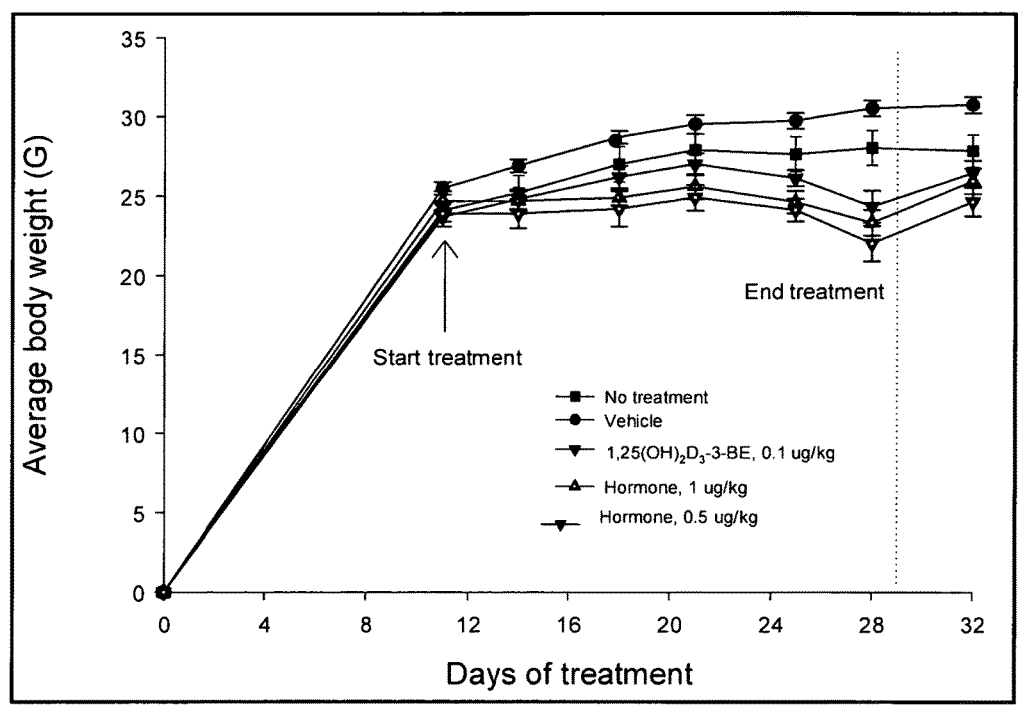
FIG. 19 depicts Effect of 1,25(OH)$_2$D$_3$-3-BE and 1,23 (OH)$_2$D$_3$ (Hormone) (q.o.d.×10, i.p.) on Body Weight in athymic DU-145 mice.

As shown in FIG. 19 AMPI-109 (0.1 µg/kg) showed some reduction in body weight which was significantly less than with calcitriol (0.5 µg/kg and 1.0 µg/kg). Another interesting observation was that after the withdrawal of AMPI-109 (day 30) weights of animals started increasing (similar to calcitriol). This is an important finding because AMPI-109 is an alkylating compound, and there may be concerns of sustained systemic toxicity.

Example 11: In Vivo Studies of AMPI-109 and Calcitriol in Nude Mice Inoculated with DU-145 Human Prostate Cancer Cells (P.O.-Administration)

Figure 20:
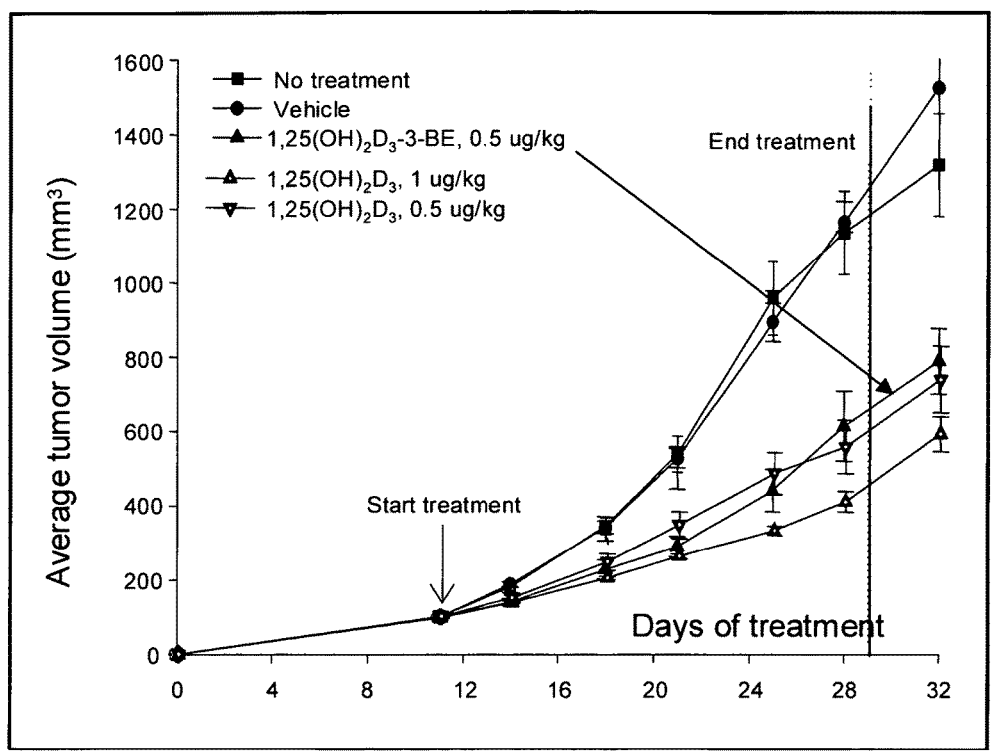
FIG. 20 depicts Effect of 1,25(OH)$_2$D$_3$-3-BE (q.o.d.×10, p.o.) on tumor volumes against tumor model DU-145 in athymic mice.
Figure 21:
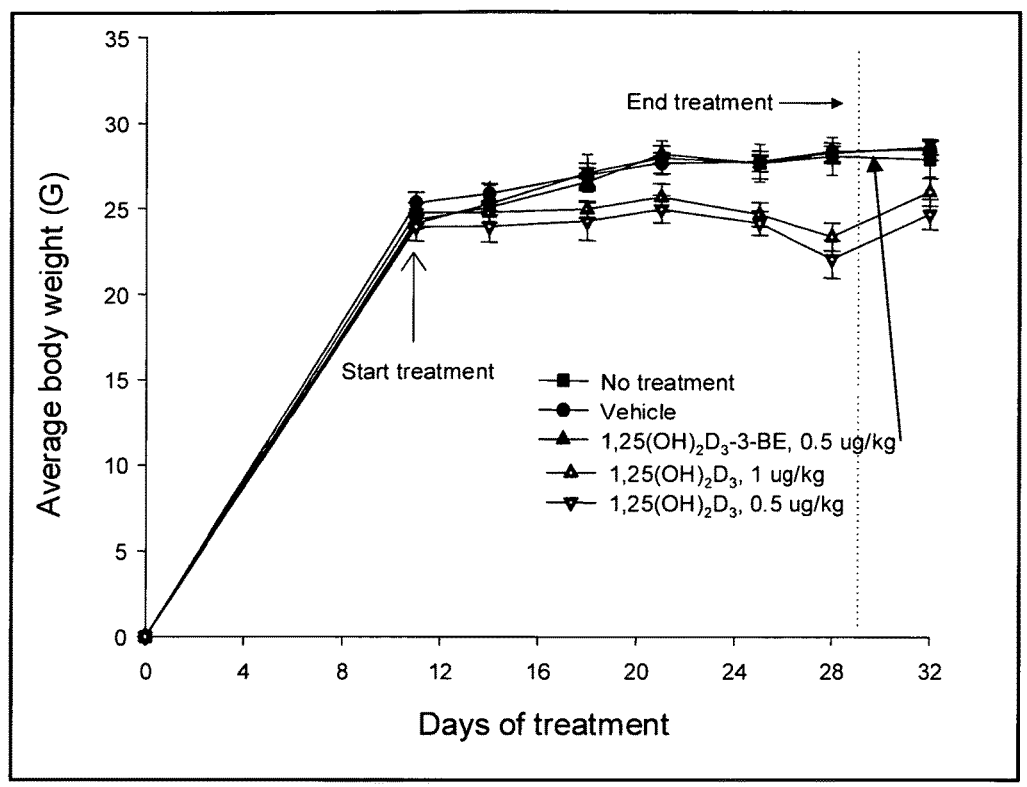
FIG. 21 depicts Effect of 1,25(OH)$_2$D$_3$-3-BE (q.o.d.×10, p.o.) on body weights in tumor model DU-145 in athymic mice.

In the p.o. administration oral gavage mode AMPI-109 (0.5 µg/kg) showed a strong anti-tumor effect (FIG. 20). This effect was similar to calcitriol (0.5 µg/kg). However, calcitriol (0.5 µg/kg and 1.0 µg/kg) caused significant loss in body weight denoting toxicity, while AMPI-109 did not cause any significant change in body weight of the animals (FIG. 19).

It is noteworthy that AMPI-109 was five (5) times less potent in the p.o.-mode than in the i.p.-mode. This is to be expected because in the i.p. mode the compound goes directly in the blood stream, while in the p.o. mode a significant portion of AMPI-109 is expected to undergo hydrolysis/metabolism before reaching the blood stream. Therefore higher amounts would be required to show any biological effect. Therapeutic agents containing hydrolysable bonds are fairly common; for example aspirin and acetaminophen contain hydrolysable ester and amine bonds.

In summary, the results described above showed strong anti-tumor activity and significant bioavailability of AMPI-109.

Example 12: In Vivo Studies of AMPI-109 and APH-0701 in Nude Mice Inoculated with DU-145 Human Prostate Cancer Cells (P.O.-Administration)

Male, athymic mice (average weight 20 gm) were fed normal rat chow and water ad libitum. They were inoculated with DU-145 cells (5×10⁶ cells, dispersed in 100 µl PBS) in the flank. When the tumor size grew to approximately 100 $mm^3$ the animals were randomized into groups of eight (8), and they were given AMPI-109 (0.5 µg/Kg in 5% DMA in sesame oil, 5% DMA in sesame oil (vehicle control), or APH-0701 (0.5 µg/Kg, in 5% DMA in sesame oil) by intraperitoneal injection (i.p.) on an average every third day (body weights were determined at each dosing). Treatment started on day 7 after tumor-implantation and was stopped on day 42, when they were sacrificed.

Figure 22:
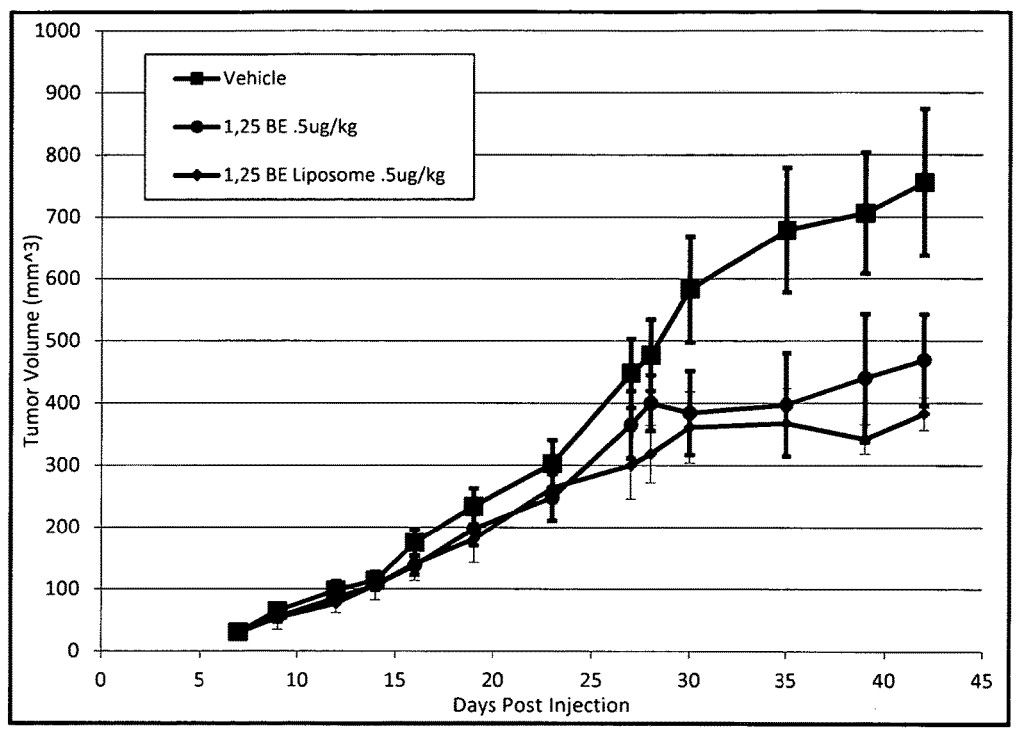
FIG. 22 depicts Tumor Size of Androgen-Insensitive Tumor (DU-145) Bearing Athymic Mice Treated with 1,25 (OH)$_2$D$_3$-3-BE, Liposomal 1,25(OH)$_2$D$_3$-3-BE and Vehicle Control.
Figure 23:
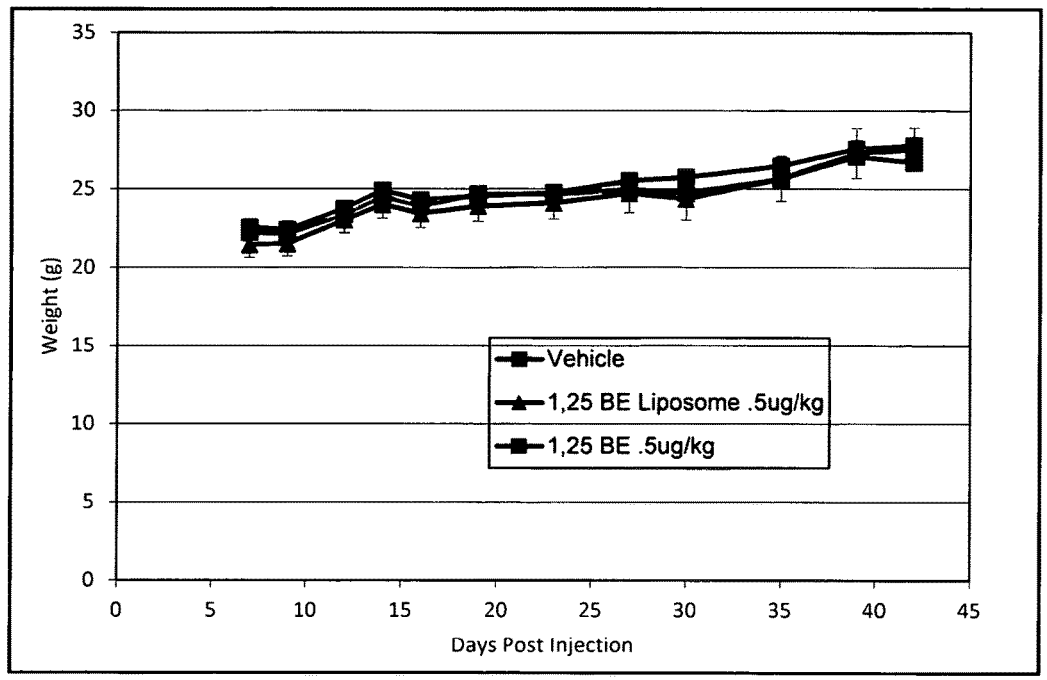
FIG. 23 depicts Body Weight of Androgen-Insensitive Tumor (DU-145) Bearing Athymic Mice Treated with 1,25 (OH)$_2$D$_3$-3-BE, Liposomal 1,25(OH)$_2$D$_3$-3-BE and Vehicle Control.

Results of our in vivo efficacy and safety study are shown in FIGS. 22 and 23. At the end of the experiment, average size of vehicle-control, AMPI-109-treated and APH-0701-treated tumors were approximately 750, 475 and 385 mm$^3$ respectively, demonstrating a strong reduction of tumor size by AMPI-109 (37% of control) and APH-0701 (49% of control), with a 33% improvement of liposomal versus naked drug (FIG. 22). On the other hand, gross body-weights of AMPI-109- and APH-0701-treated animals were not significantly different from control animals, indicating lack of toxicity (FIG. 23). Therefore, collectively these results demonstrated that AMPI-109 and APH-0701 have a strong translational potential as a therapeutic agent in androgen-insensitive prostate cancer.

Example 13: Antiproliferation Studies of Normal and Cancerous Cell Lines Treated with AMPI-105 or Bioactive Vitamin D$_3$ Hormone Antiproliferation studies of keratinocytes (normal skin), MCF-7 (breast cancer), PZ-HPV-7 (immortalized normal prostate), LNcap (androgen-sensitive prostate cancer) and PC-3 (androgen-insensitive prostate cancer) cells, treated with $10^{-6}$M of 25-OH-D$_3$-3-BE (AMPI-105) or 1,25 (OH)$_2$D$_3$ (bioactive Vitamin D$_3$ hormone) were performed with a $^3$H-thymidine incorporation assay Growth-inhibitory effect of 1,25(OH)$_2$D$_3$ and its analogs is known to vary among cell-lines and even among lines from the same tissue. But, in general, strongest effect is observed at a $10^{-6}$M concentration of the hormone or its analogs. Although this concentration is considered to be physiologically irrelevant, it produces optimal effect. Therefore, this dose was used for screening of various cell lines.

PZ-HPV-7 cells were grown in MCDB media containing pituitary extract, epidermal growth factor (EGF) and 1% penicillin/streptomycin. Keratinocytes were also grown in the same media with additional PG1 and insulin. PC-3, LNCaP, DU-145 cells were grown in RPMI media containing 10% fetal bovine serum (FBS) and antibiotics. MCF-7 cells were grown in DMEM media containing 10% FBS and antibiotics. LAPC-4 cells were maintained in IMEM media containing antibiotics, 1° % L-glutamine and 10 nM of R1881, a synthetic progestin. MC3T3 mouse bone cells were grown in α-MEM media containing 10% FBS and antibiotics. In general, cells were grown in 35 mm dishes to 70-80% confluence and then plated into 24-well plates in respective media. After the cells grew to approximately 70% confluence, they were serum-starved for 20 hours (MCF-7, PC-3, LNCaP and DU-145 cells) followed by incubation with steroid samples. Keratinocytes and PZ-HPV-7 cells, after reaching 70% confluence, were kept in MCDB media without additives for 20 hours before treatment with steroids. In general, reagents were dissolved in ethanol (EtOH), and dilution with the media was adjusted in such a way that the concentration of EtOH was 0.1% v/v.

Assays were carried out with six (6) replicates and student's t-test was employed for statistical analysis. Results are expressed relative to EtOH (100%) in FIG. 24.

Figure 24:
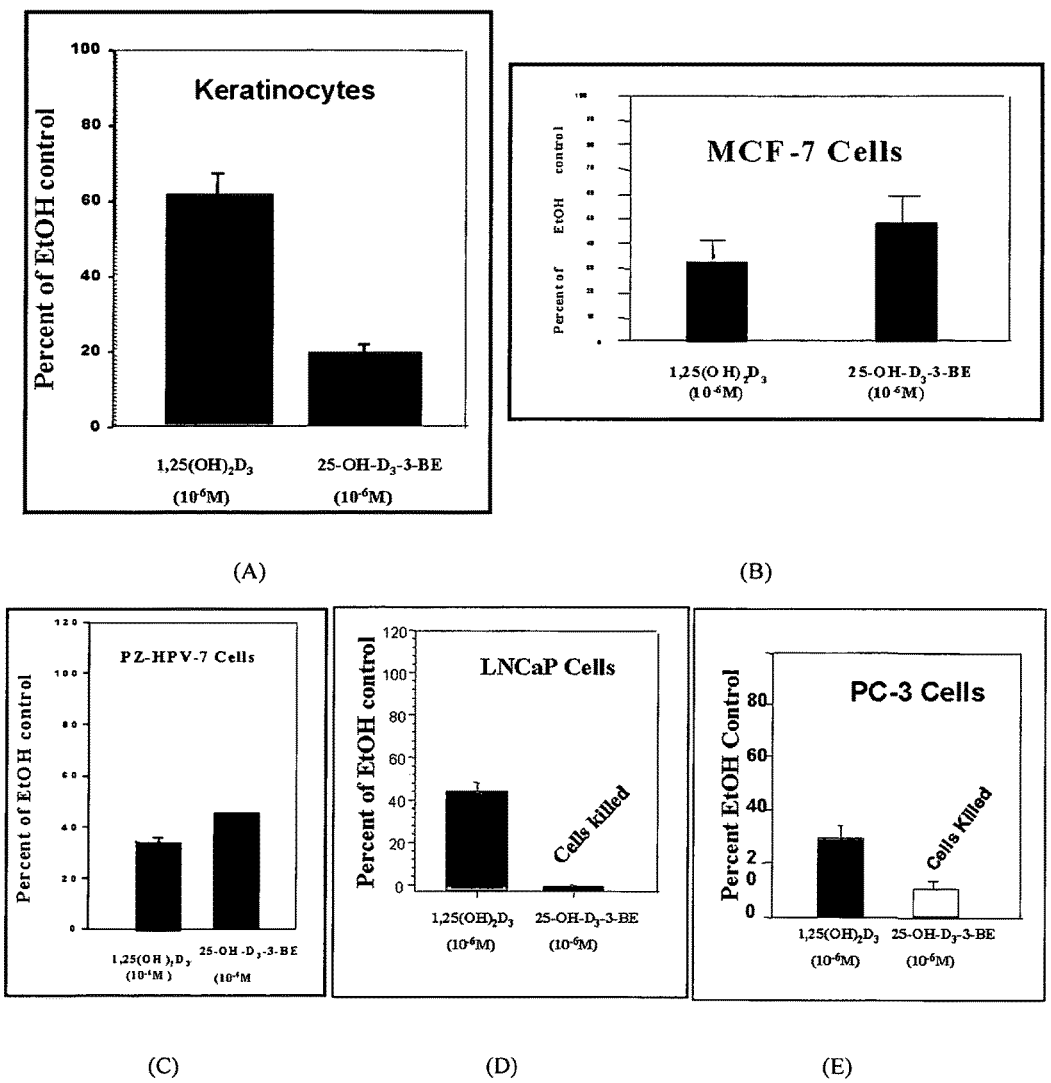
FIG. 24 depicts $^3$H-Thymidine Incorporation Assays of Keratinocytes, MCF-7, PZ-HPV-7, LNCaP and PC-3 Cells.

As shown in FIG. 24-E, $10^{-6}$ M of 25-OH-D$_3$-3-BE and 1,25(OH)$_2$D$_3$ inhibited the growth of all the cells with varying efficiency. However, the effect of 25-OH-D$_3$-3-BE was strongest in LNCaP and PC-3 prostate cancer cells.

For example, growth of LNCaP cells were inhibited by approximately 60% and 98% with 1,25(OH)$_2$D$_3$ and 25-OH-D$_3$-3-BE, respectively (FIG. 24-D), while growth of PC-3 cells was reduced by 70% and 90% by 1,25(OH)$_2$D$_3$ and 25-OH-D$_3$-3-BE, respectively (FIG. 24-E). In contrast, growth of normal immortalized prostate cells (PZ-HPV-7 cells) were inhibited by approximately 50% and 65% by $10^{-6}$ M of 25-OH-D$_3$-3-BE and $10^{-6}$ M of 1,25(OH)$_2$D$_3$, respectively (FIG. 24-C).

While growth inhibition by 25-OH-D$_3$-3-BE was stronger than an equivalent amount of 1,25 (OH)$_2$D$_3$ in keratinocytes (FIG. 24-A), the effect of 25-OH-D$_3$-3-BE was weaker than 1,25(OH)$_2$D$_3$ in MCF-7 breast cancer cells (FIG. 24-B). Furthermore, $10^{-6}$ M of 25-OH-D$_3$ showed marginal antiproliferative effect in PC-3 cells (FIG. 24-F). We also observed that $10^{-6}$ M of 25-OH-D$_3$-3-BE was cytotoxic only to LNCaP and PC-3 cells, causing the cells to lift, float and die, as seen under a phase contrast microscope.

Figure 25:
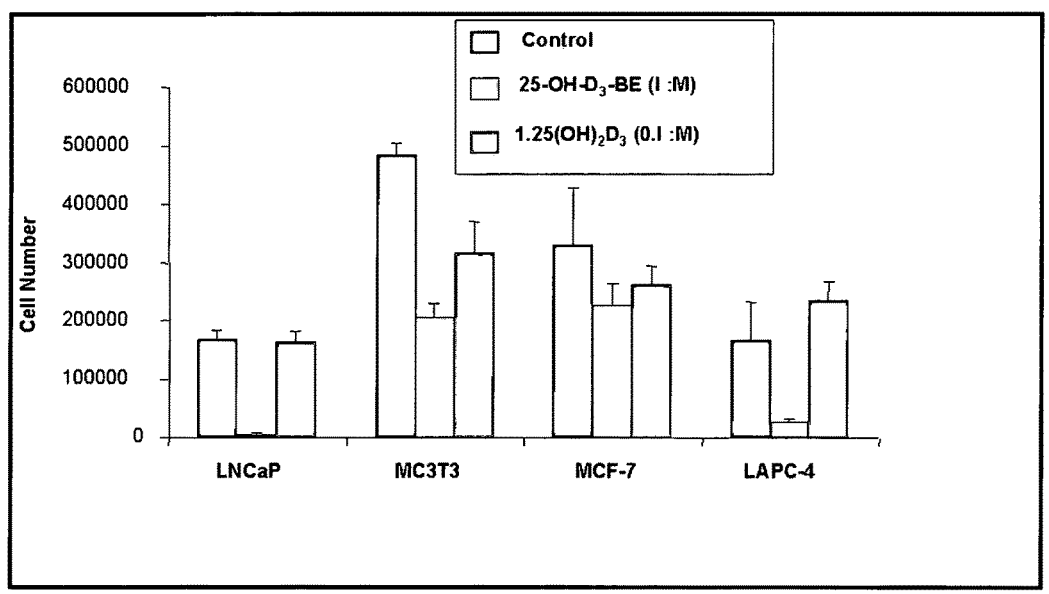
FIG. 25 depicts Cell Counting Assay of LAPC-4, LNCaP, MCF-7 and MC3T3 Cells Treated with 25-OH-$D_3$-BE or 1,25(OH)$_2$D$_3$.

In a cell counting assay, LNCaP and LAPC-4 cells had sharply reduced number of cells with $10^{-6}$ M of 25-OH-D$_3$-3-BE after 24 hours incubation (FIG. 25) while MCF-7 and MC3T3 cells (incubated for 48 hr) were affected to a much lesser extent than for LNCaP and LAPC-4 cells, although the effect on MC3T3 cells was significantly stronger than in MCF-7 cells. It should be noted that in this assay cells were not serum-starved prior to addition of the reagents, and $10^{-7}$ M of 1,25(OH)$_2$D$_3$ had little effect on all the cells. $10^{-7}$ M of 1,25(OH)$_2$D$_3$ was shown to produce a significant effect in LNCaP cells after a longer period (3-6 days) of incubation.

Example 13: Efficacy Study of 25-OH-D$_3$-3-BE in Athymic Nude Mice

Male, athymic nude mice (average weight 20 gm) were fed normal rat chow and water ad libitum. They were inoculated with DU 145 cells, grown in culture, in the flank under light anesthesia. After the tumor size grew to approximately 100 mm$^3$, the animals were randomized into three (3) groups of ten (10) tumor-bearing animals and they were given 25-OH-D$_3$-3-BE (0.25 and 0.5 mg/kg, dissolved in 5% DMA in sesame oil) or left untreated. Administration of the compound was done by oral gavage on every third day (when weights were determined). Treatment started on day 11 and stopped on day 31; and they were left untreated for several additional days (as shown in FIG. 26) when they were sacrificed and blood was collected.

Figure 26:
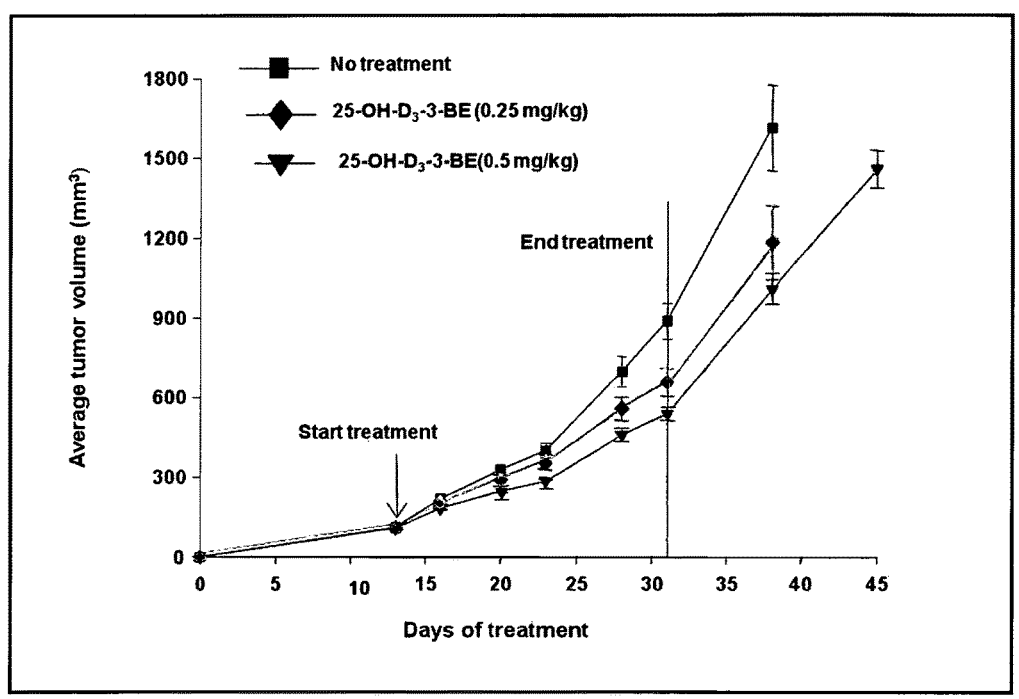
FIG. 26 depicts Effect of 25-OH-$D_3$-3-BE (every 3 days, starting on day 11 and ending on day 31, p.o.) on tumor volumes against tumor model DU-145 in athymic mice.
Figure 27:
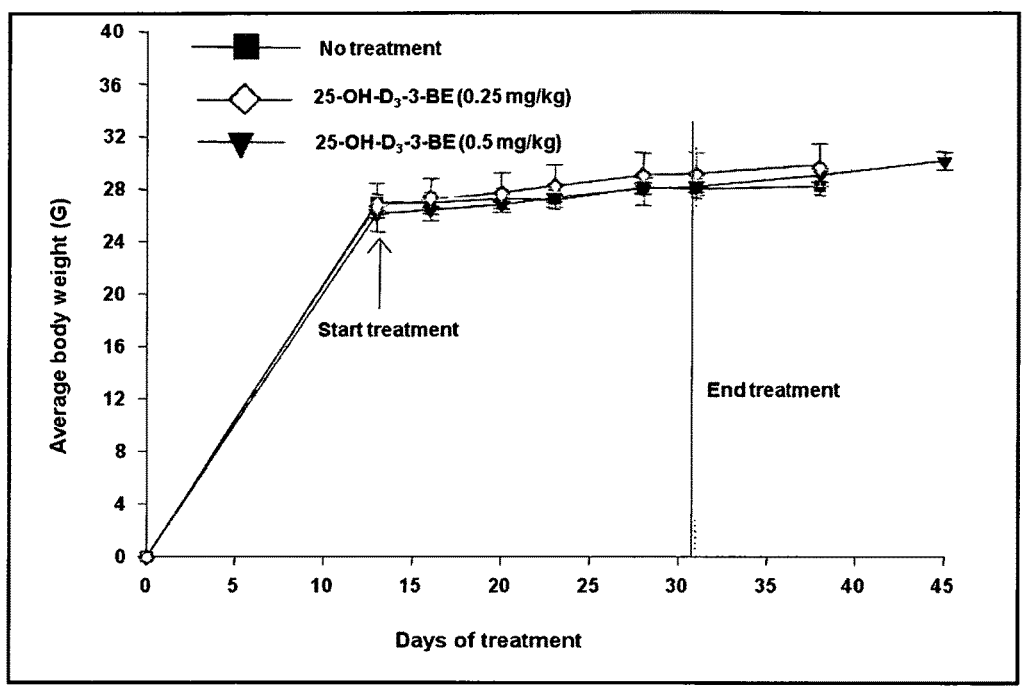
FIG. 27 depicts Effect of 25-OH-$D_3$-3-BE (every 3 days, starting on day 11 and ending on day 31, p.o.) on body weights of tumor model DU-145 in athymic mice.

25-OH-D$_3$-3-BE showed a dose-dependent anti-tumor effect at 0.25 and 0.5 mμg/kg doses (FIG. 26). For example, at the end of treatment average size of the untreated tumor was approximately 900 mm$^3$, while average tumor volumes were 650 mm$^3$ and 500 mm$^3$ with 0.25 and 0.5 μg/kg of 25-OH-D$_3$-3-BE respectively. Toxicity was measured by following gross weight of the animals during and after the treatment. As shown in FIG. 27 there was no significant difference between the 25-OH-D$_3$-3-BE-treated and untreated animals. It is to be noted that these results are preliminary in nature and we plan to carry out more extensive dose-response studies both by oral gavage administration mode as well as determination of serum-calcium levels in the proposed studies.

Example 15: Viability Testing of Vitamin AMPI-107 and Calcitrol in Normal Prostate Cells by MTT Reduction Vitamin D epoxide (AMPI-109) was received at a concentration of $10^{-2}$M (diluting 1000-fold to give $10^{-5}$M, and a later 10× dilution produced $10^{-6}$M. The hormone [1,25

(OH)$_2$D$_3$] or Calcitrol positive control sample was received at a concentration of 10$^{-3}$M. A 1000-fold dilution gave 10$^{-6}$M.

Normal prostate WPMY cells were cultured to confluency in 10% fetal calf serum supplemented Dulbecco's modified Eagle's medium plus 1% antibiotic/antimycotic in 96 well dishes and at confluency, cells were exposed to 1 µM Calcitrol, 1 and 10 µM AMPI-107 in complete medium for 24 hours.

Cells were then incubated with yellow tetrazolium MTT (3-(4,5-dimethyl thiazolyl-2)-2,5-diphenyltetrazolium bromide) for 3 h and was then extracted in acid isopropanol (0.1 N HCl in anhydrous isopropanol). MTT is reduced in metabolically active cells, in part by the action of dehydrogenase enzymes, to generate reducing equivalents such as NADH and NADPH. The resulting intracellular purple formazan can be solubilized and quantified by spectrophotometry. After 5 minutes at room temperature, absorbances in plates were measured using a plate analyzer set for in dual wavelength comparisons at wavelength of 540 nm with a reference wavelength of 620 nm.

Figure 28:
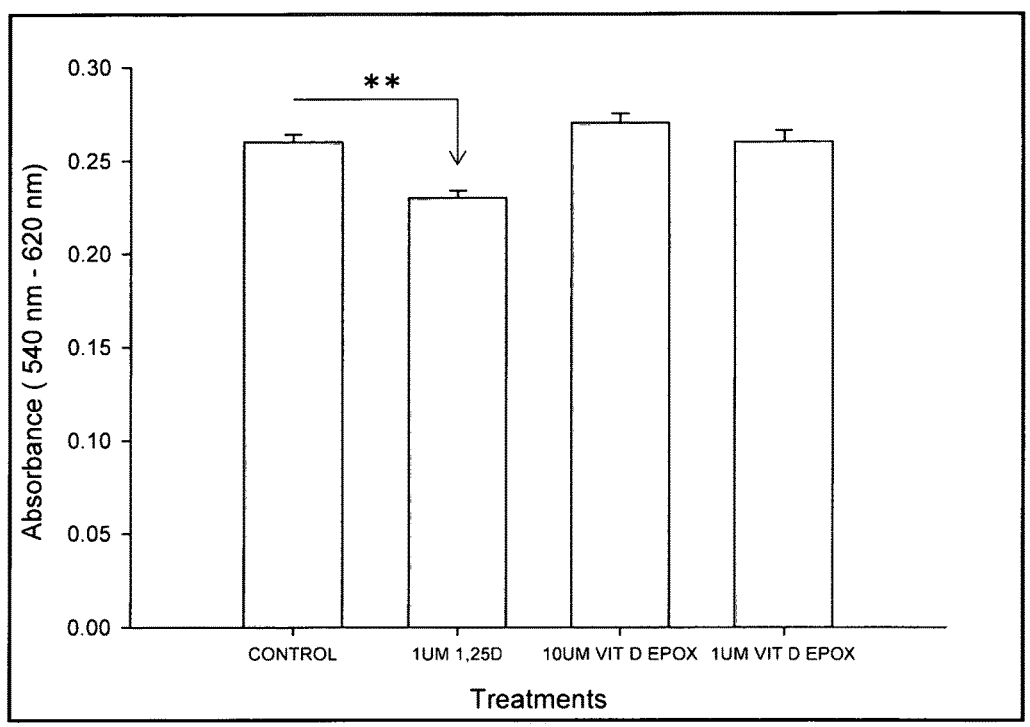
FIG. 28 depicts Effect of 24 h Treatment on WPMY-1 Cells (Mean and SEM) by AMPI-107 and Calcitrol.

Compared to control cells, FIG. 28, AMPI-107 at 1 and 10 µM did not significantly depress cell metabolism. By comparison, 1 µM Calcitrol did slightly, but significantly reduce cell metabolism (**p<0.01, one way ANOVA with Bonferroni post-testing).

Example 16: Antiproliferative Evaluation of AMPI-107 Versus Calcitrol in Prostate Cancer Cells Prostate cancer cells (DU-145, PC-3 and LNCaP) were grown in DMEM medium with 10% FBS, antibiotics, etc. When the confluence reached approximately 50% they were dosed with ethanolic solutions (0.1% in media) with various doses of either AMPI-107 or the hormone [1,25(OH)$_2$D$_3$] aka Calcitrol or ethanol (control) on days 1, 3 and 5, and cells were counted on a hemocytometer on the 7$^{th}$ day. Results are designated as percentage of ethanol control.

Figure 29:
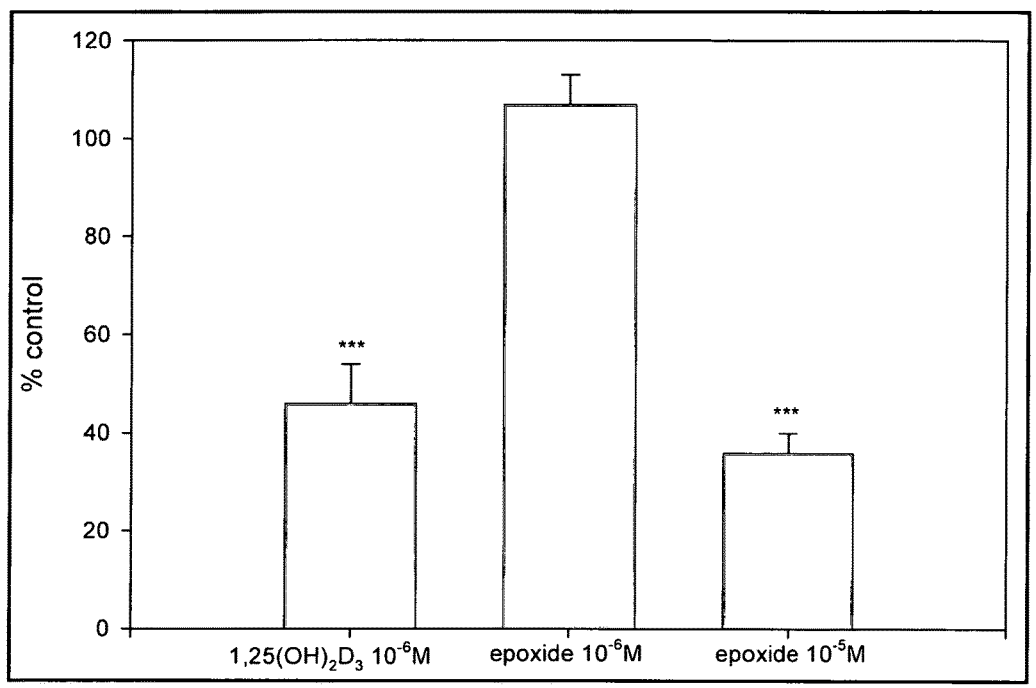
FIG. 29 depicts Antiproliferative evaluation of AMPI-107 vs. Calcitrol in DU-145 Prostate Cancer Cells.

As shown in FIG. 29, Calcitrol (10$^{-6}$M) and AMPI-107 (10$^{-5}$M) had approximately similar growth inhibitory activity in DU-145 cells.

Figure 30:
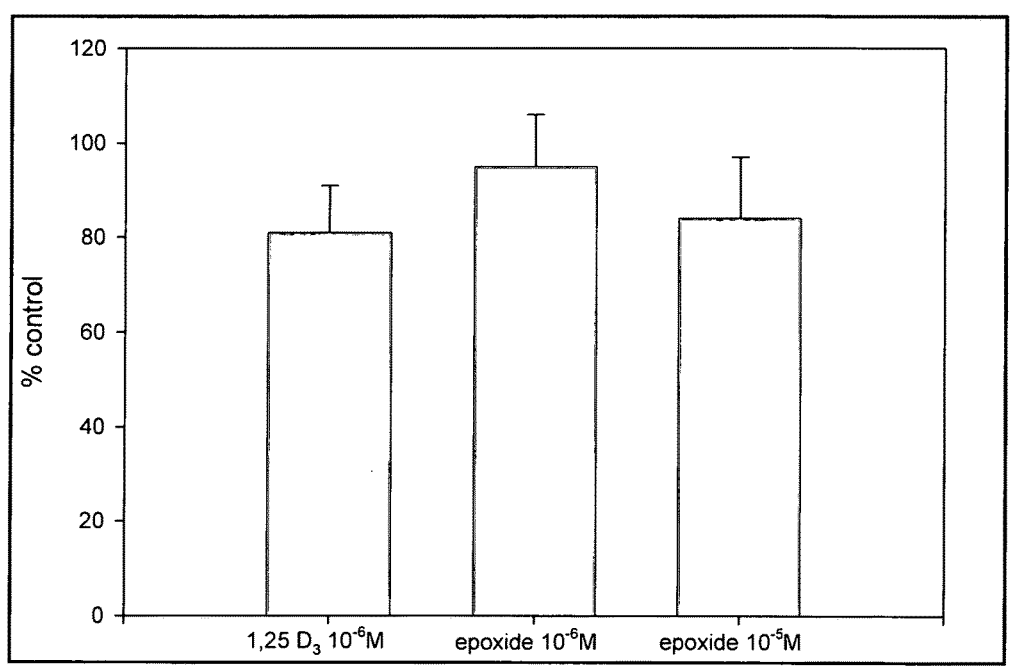
FIG. 30 depicts Antiproliferative evaluation of AMPI-107 vs. Calcitrol in LNCaP Prostate Cancer Cells.

As shown in FIG. 30, Calcitrol (10$^{-6}$M) and AMPI-107 (10$^{-5}$M) strongly inhibited the growth of LNCaP cells, but AMPI-107 had a significantly stronger effect at this dose.

Figure 31:
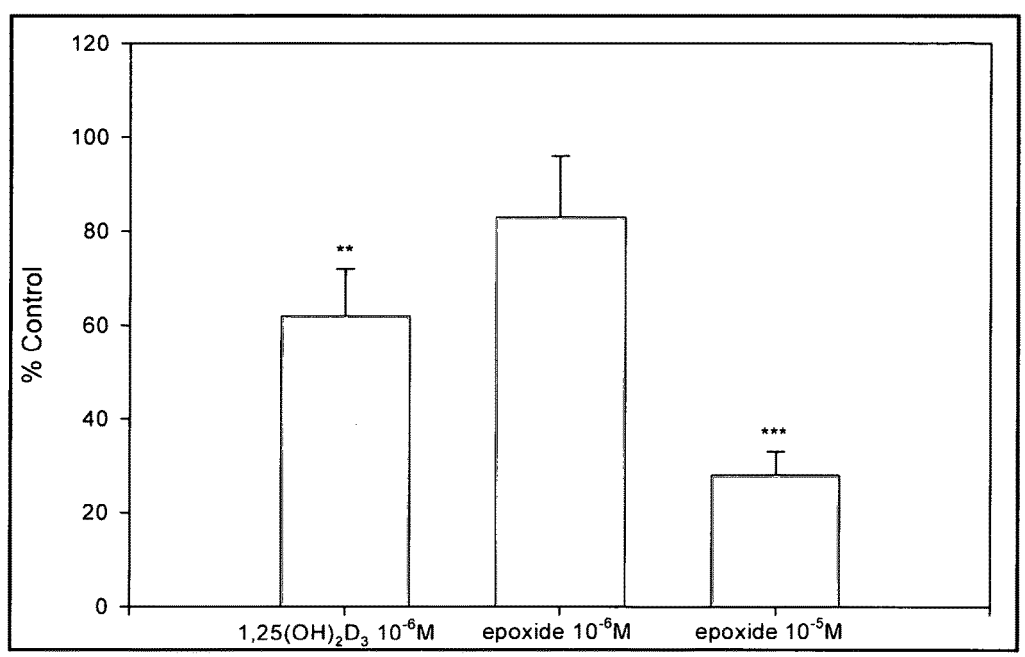
FIG. 31 depicts Antiproliferative evaluation of AMPI-107 vs. Calcitrol in PC-3 Prostate Cancer Cells.

As shown in FIG. 31, Calcitrol (10-M) and AMPI-107 (10$^5$M) strongly inhibited the growth of PC-3 cells, but AMPI-107 had a significantly stronger effect at this dose.

Cell-counting assay (dosing on 1$^{st}$, 3$^{rd}$, and 5$^{th}$ days, harvesting and counting on 7$^{th}$ day) demonstrated that AMPI-107 is either equally effective (DU-145 and PC-3 cells) or more (LNCaP cells) than Calcitrol. However, concentration of AMPI-107 was 10-times higher than Calcitrol.

Example 17: In Vivo Studies of AMPI-107 in Nude Mice Inoculated with DU-145 Human Prostate Cancer Cells (P.O. and I.P. Administration)

Male, athymic mice (average weight 20 gm) were fed normal rat chow and water ad libitum. They were inoculated with DU 145 human androgen-insensitive prostate cancer cells (10$^6$), grown in culture in the flank under light anesthesia. When the tumor size grew to approximately 100 mm$^3$ the animals were randomized into groups of ten (10) tumor-bearing animals, and they were given vitamin D$_3$-3-epoxide, AMPI 107 (1 mg/kg), 1,25(OH)$_2$D$_3$ hormone (0.5 and 1.0 µg/kg), and vehicle (5% DMA in sesame oil) by intraperitoneal injection (i.p.) or by oral gavage (p.o.) on every third day (when body weights were determined); and one group was left untreated. Treatment started on day 11 and stopped on day 30; and they were left untreated for two (2) additional days when they were sacrificed. The i.p. results are respectively shown in FIGS. 32 and 33 for the effect of AMPI-107 and the 1,25(OH)$_2$D$_3$ hormone on tumor growth and body weight. The p.o. results are respectively shown in FIGS. 34 and 35 for the effect of AMPI-107 and the 1,25(OH)$_2$D$_3$ hormone on tumor growth and body weight. Note AMPI-107 is referred to as MPI-107 in these figures.

Figure 32:
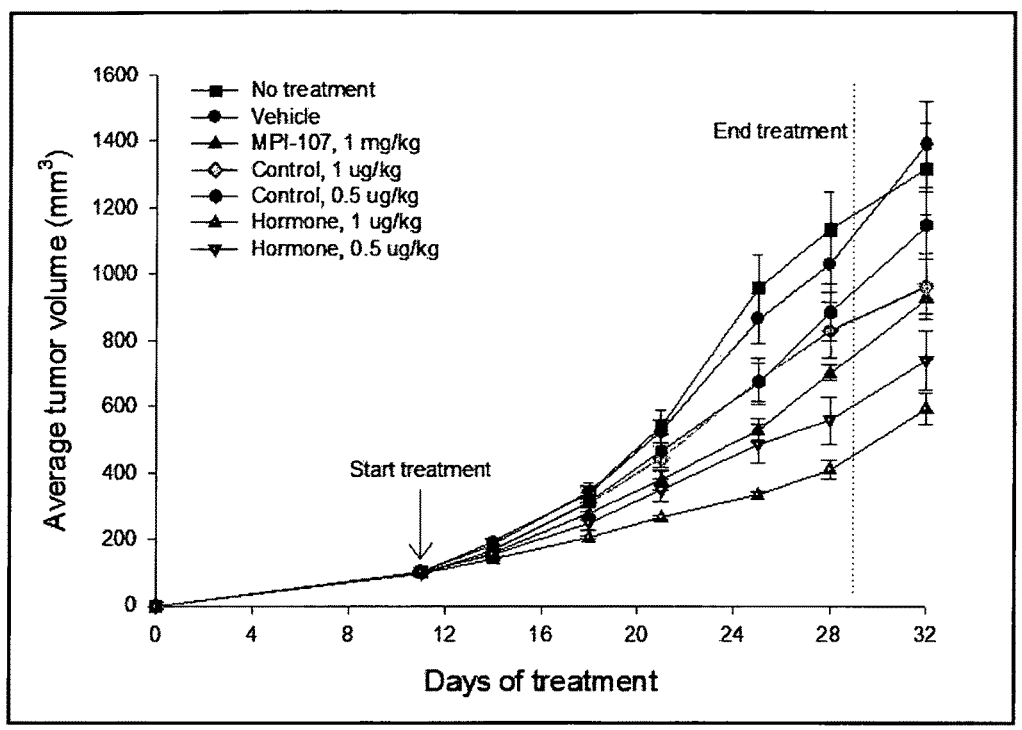
FIG. 32 depicts Effect of AMPI-109 (Vitamin $D_3$-3-epoxide [$D_3$-3-EPO]) vs Calcitriol (1,25(OH)$_2$D$_3$) (q.o.d.× 10, i.p.) on tumor volumes against tumor model DU-145 in athymic mice.
Figure 33:
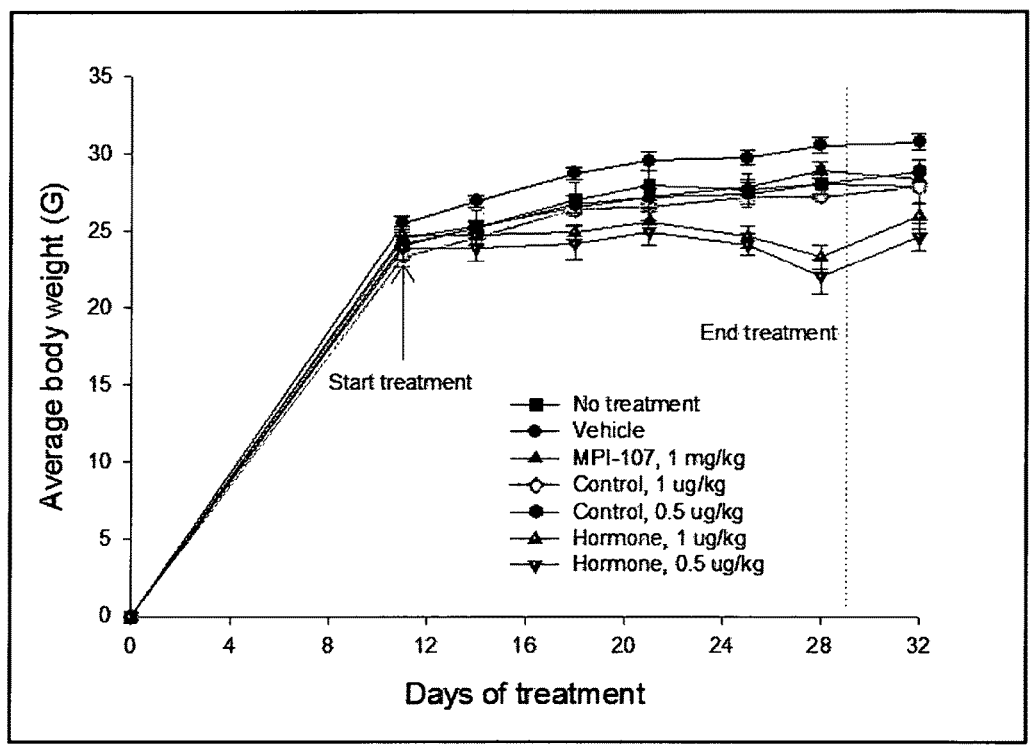
FIG. 33 depicts Effect of AMPI-109 (Vitamin $D_3$-3-epoxide [$D_3$-3-EPO]) vs Calcitriol (1,25(OH)$_2$D$_3$) AMPI-017 (q.o.d.×10, i.p.) on body weights of tumor model DU-145 in athymic mice.
Figure 34:
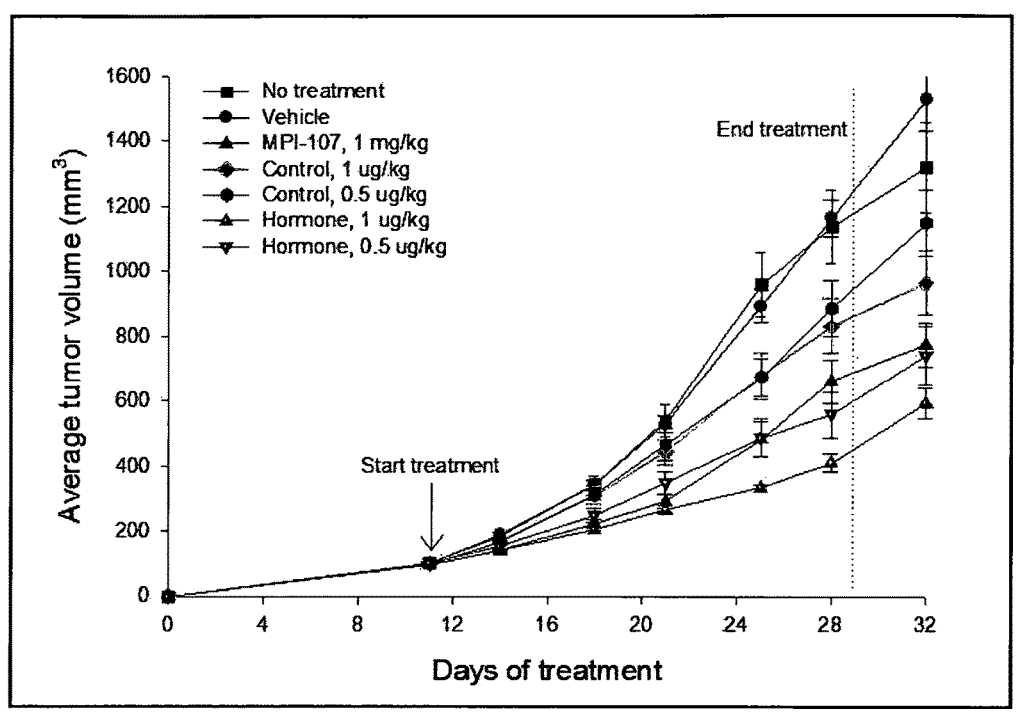
FIG. 34 depicts Effect of AMPI-109 (Vitamin $D_3$-3-epoxide [$D_3$-3-EPO]) vs Calcitriol (1,25(OH)$_2$D$_3$) (q.o.d.× 10, p.o.) on tumor volumes against tumor model DU-145 in athymic mice.
Figure 35:
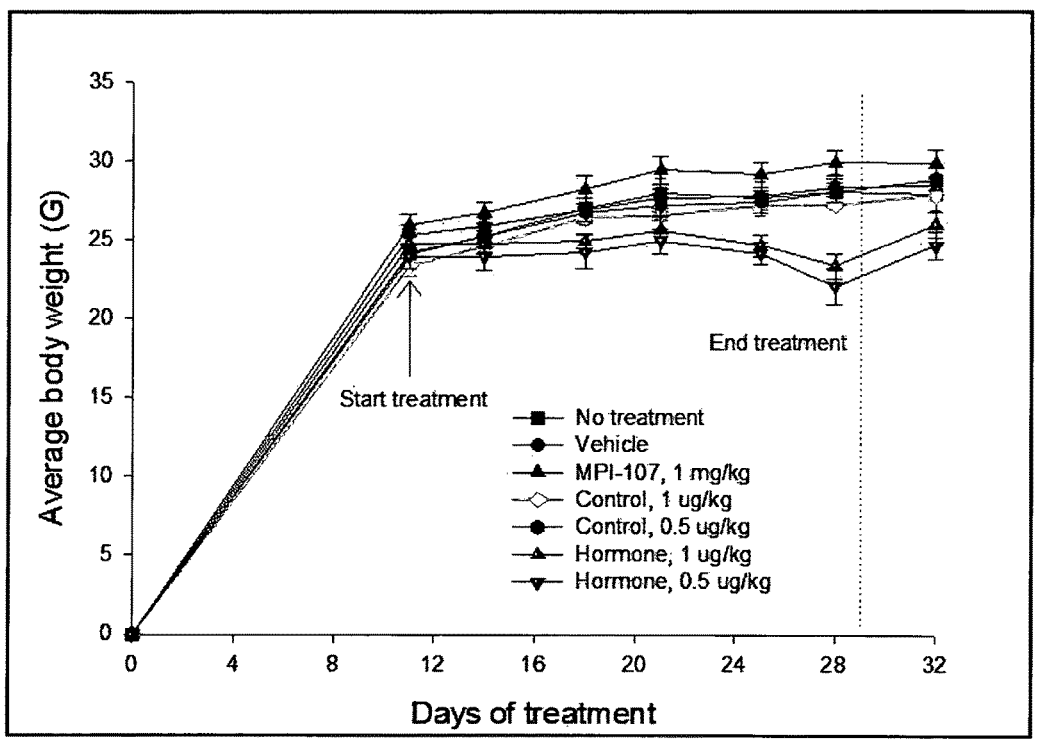
FIG. 35 depicts Effect of AMPI-109 (Vitamin $D_3$-3-epoxide [$D_3$-3-EPO]) vs Calcitriol (1,25(OH)$_2$D$_3$) AMPI-017 (q.o.d.×10, p.o.) on body weights of tumor model DU-145 in athymic mice.

In terms of efficacy vitamin D$_3$-3-epoxide, MPI 107 (1 mg/kg) was similar to hormone (0.5 µg/kg) in both i.p. and p.o. administration modes (FIGS. 32 and 34). But 1,25(OH)$_2$D$_3$, hormone (0.5 and 1.0 µg/kg) was clearly toxic as evidenced by considerable loss of body weight in both cases, while vitamin D$_3$-3-epoxide, MPI 107 was completely nontoxic (FIGS. 33 and 35).

Surprisingly, the results of this study demonstrated that vitamin D$_3$-3-epoxide strongly reduced tumor size in this model both in i.p. and p.o. administration modes without any significant toxicities.

The APH-0701 nanosomal formulation of AMPI-105 will have a similar impact to that shown in Example 4 of reducing its toxicity and increasing its efficacy.

Example 18: Polymeric Nanoencapsulation of Vitamin D$_3$ Analogs

Polymeric Spheres were formed which contained the Vitamin D$_3$ analogs in the following manner. A feed rate of 0.25 mg/ml Vitamin D$_3$ analog in an ethanolic buffer solution and a supercritical, critical or near critical solution of solution of poly(D,L-lactic acid), poly(glycolic acid) in propane was injected into a decompression fluid of deionized water and produced a batch of spheres having a mean particle diameter of 200 to 400 nanometers. The polymer solution was maintained prior to injection at a pressure of 21 MPa and 30 degrees centigrade.

This suspension of spheres in a phosphate buffer was then lyophilized. Dried spheres were stored at five degrees centigrade until used or compressed into tablets. Prior to use, dried spheres were re-constituted and formulated into a phosphate buffer solution.

Example 19: Oil Capsule Formulation of Vitamin D$_3$ Analogs

The Vitamin D$_3$ analogs are formulated in different doses ranging from 500 IU to 5,000 IU in gel capsules containing the following.
   500 IU to 5,000 IU of Vitamin D$_3$ analogs
   30 mg of mixed tocopherol 90% as an antioxidant [10.7%]
   30 mg of Lecithin as an emulsifier to improve solubility and bioavailability [10.7%]
   15 mg of Medium Chain Triglyceride (MCT) as a co-emulsifier [5.4%]
   175 mg of Olive Oil as an excipient with some nutritional value [62.5%]; Nitrogen head Example 20: Water Capsule Formulation of Vitamin D$_3$ Analogs The Vitamin D$_3$ analogs are formulated in different doses ranging from 500 IU to 5,000 IU in gel capsules containing the following: Medium Chain Triglyceride (MCT) as a co-emulsifier, Lecithin Soy, Hydroxyl Propyl Methyl Cellulose (HPMC) and Purified Water.

What is claimed is:

1. A method of treating a disease responsive to Vitamin D3 or Vitamin D3 analog, wherein the disease is a prostate cancer or a kidney cancer, comprising the steps of:
   a. providing a medicament having a plurality of nanosomes having at least one bilayer of phospholipid in which Vitamin $D_3$-3-bromoacetate [$D_3$-3-BE] or Vitamin $D_3$-3-epoxide [$D_3$-3-EPO] is distributed; and
   b. administering an amount of medicament having an effective amount of $D_3$-3-BE or $D_3$-3-EPO to treat the disease.

2. The method of claim 1 wherein said disease is a prostate cancer.

3. A method of treating a disease responsive to Vitamin D3 or Vitamin D3 analog, wherein the disease is a prostate cancer or a kidney cancer, comprising the steps of:
   a. providing a gel capsule having a gelatin outer layer defining an inner volume and having an oil base contained in said inner volume, and further comprising Vitamin $D_3$-3-bromoacetate [$D_3$-3-BE] or Vitamin $D_3$-3-epoxide [$D_3$-3-EPO] dissolved in said oil base; and
   b. administering an effective amount of $D_3$-3-BE or $D_3$-3-EPO by ingesting one or more gel capsules.

4. The method of claim 3 wherein said disease is a prostate cancer.

* * * * *